United States Patent
Freed et al.

(10) Patent No.: US 10,087,417 B2
(45) Date of Patent: Oct. 2, 2018

(54) THREE-DIMENSIONAL MODEL OF HUMAN CORTEX

(71) Applicants: William J. Freed, Bowie, MD (US); Chun-Ting Lee, Miami, FL (US)

(72) Inventors: William J. Freed, Bowie, MD (US); Chun-Ting Lee, Miami, FL (US)

(*) Notice: Subject to any disclaimer, the term of this patent is extended or adjusted under 35 U.S.C. 154(b) by 221 days.

(21) Appl. No.: 15/136,250

(22) Filed: Apr. 22, 2016

(65) Prior Publication Data

US 2016/0312181 A1   Oct. 27, 2016

Related U.S. Application Data

(60) Provisional application No. 62/151,243, filed on Apr. 22, 2015.

(51) Int. Cl.
*C12N 5/079*   (2010.01)

(52) U.S. Cl.
CPC ...... *C12N 5/0618* (2013.01); *C12N 2501/115* (2013.01); *C12N 2501/119* (2013.01); *C12N 2501/155* (2013.01); *C12N 2501/91* (2013.01); *C12N 2503/04* (2013.01); *C12N 2506/02* (2013.01); *C12N 2506/45* (2013.01); *C12N 2513/00* (2013.01)

(58) Field of Classification Search
CPC ............ C12N 5/0618; C12N 2501/115; C12N 2501/119; C12N 2501/155; C12N 2501/91; C12N 2503/04; C12N 2506/02; C12N 2506/45; C12N 2513/00
See application file for complete search history.

(56) References Cited

U.S. PATENT DOCUMENTS

2015/0361393 A1   12/2015   Nicholas et al.

FOREIGN PATENT DOCUMENTS

| EP | 2497825 | 9/2012 |
|---|---|---|
| WO | WO 2010/144696 | 12/2010 |
| WO | WO 2012/013936 | 2/2012 |
| WO | WO 2014/090993 | 6/2014 |
| WO | WO 2014/152321 | 9/2014 |
| WO | WO 2015/069736 | 5/2015 |

OTHER PUBLICATIONS

TGF-beta/Smad signaling pathway. https://www.cellsignal.com/contents/science-cst-pathways-stem-cell-markers/tgf-smad-signaling-interactive-pathway/pathways-tgfb on Jan. 29, 2018, p. 1.*
Ornitz et al., WIREs Dev. Biol., 4: 215-266, 2015.*
Thomson et al., Science 282: 1145-147, 1998.*
Cao et al., J. of Exp. Zoo., 311A: 368-376, 2009.*
Brevini et al., Theriogenology, 74: 544-550, 2010.*
Paris et al., Theriogenology, 74: 516-524, 2010.*
Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Chambers et al., Nature Biotechnology, 27(3): 275-280, 2009.*
Greber et al., The EMBO Journal, 30: 4874-4884, 2011.*
Kindberg et al., "An in vitro model of human neocortical development using pluripotent stem cells: cocaine-induced cytoarchitectural alterations," *Disease Models & Mechanisms*, vol. 7, pp. 1397-1405, 2014.
Lancaster et al., "Cerebral organoids model human brain development and microcephaly," *Nature*, vol. 501, pp. 373-379, 2013 (author manuscript version, 21 pages).
Muratore et al., "Comparison and Optimization of hiPSC Forebrain Cortical Differentiation Protocols," *PLoS One*, vol. 9, No. 8, e105807, 2014 (18 pages).

* cited by examiner

*Primary Examiner* — Thaian N Ton
(74) *Attorney, Agent, or Firm* — Klarquist Sparkman, LLP

(57) ABSTRACT

Disclosed herein are methods for differentiation of neuronal cells from stem cells, which produce a three-dimensional model of the neocortex structure. In some embodiments, the methods include culturing stem cells with at least one inhibitor of SMAD signaling and at least one inhibitor of fibroblast growth factor signaling for a period of time to result in formation of an embryoid body. The embryoid body is then cultured with at least one FGF (for example, basic FGF) for a period of time sufficient to produce a neuroepithelial (NE) rosette. The rosette is then isolated and cultured in suspension or adherent culture in the presence of at least one FGF for a period of time sufficient to produce cells with dorsal cortical identity and those cells are then cultured in the substantial absence of trophic factors for a period of time sufficient to form a neocortical organoid.

15 Claims, 18 Drawing Sheets
Specification includes a Sequence Listing.

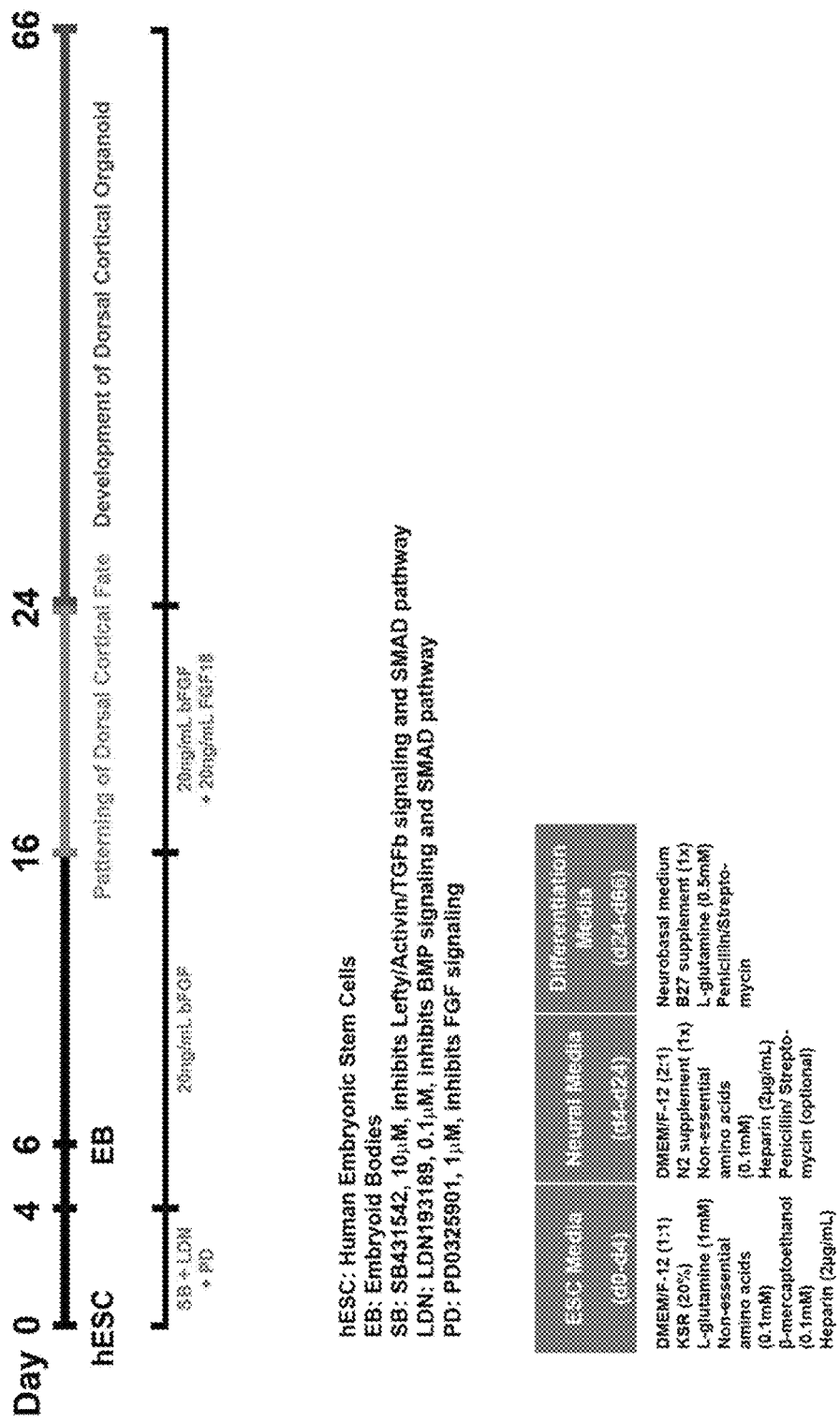

FIG. 4A
FIG. 4B
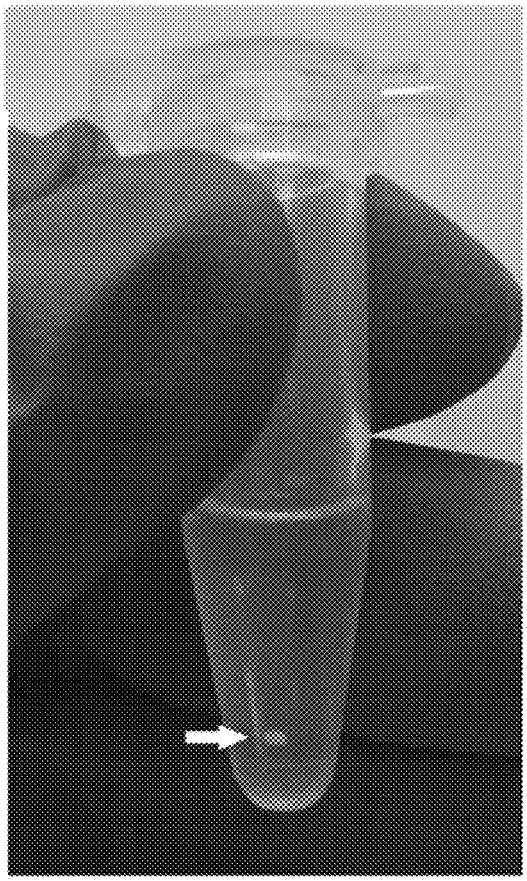
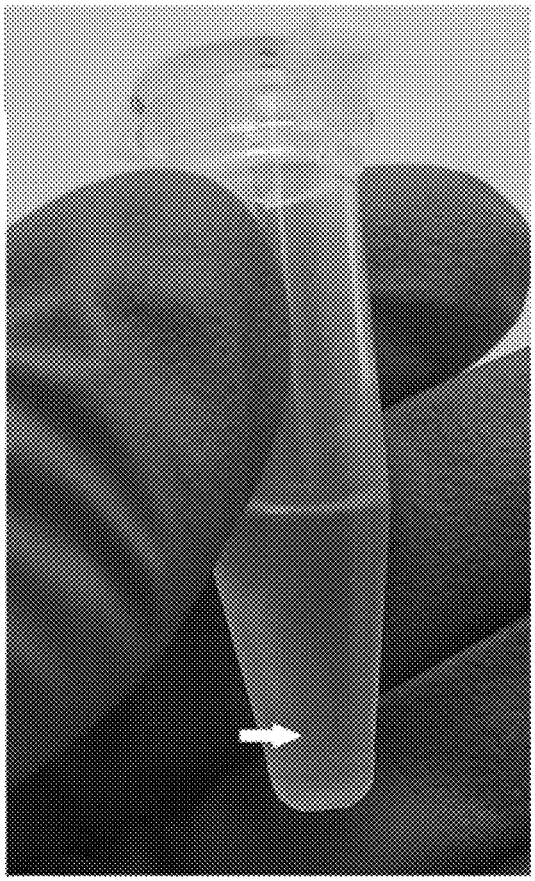
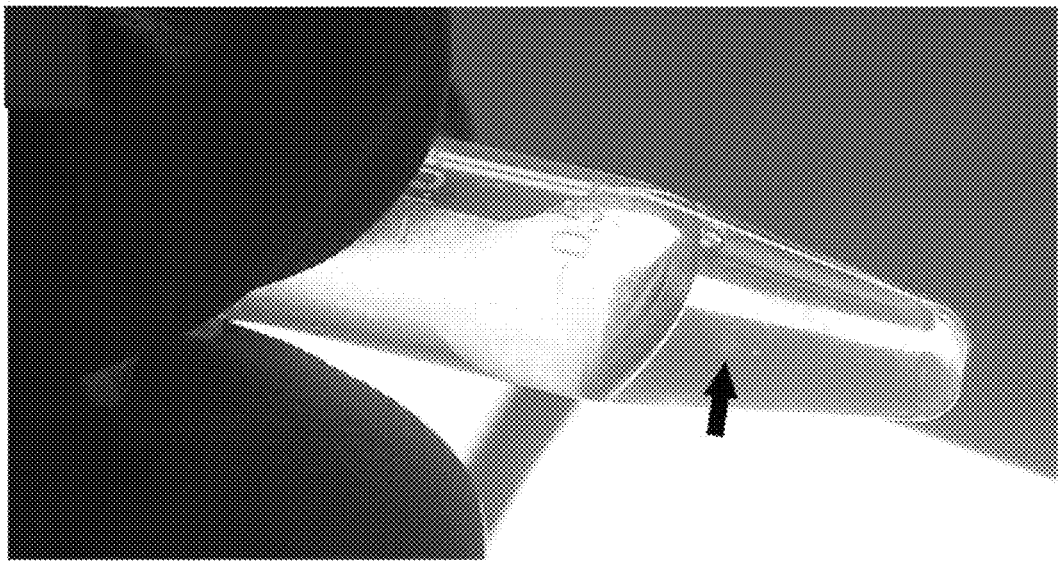
FIG. 4C

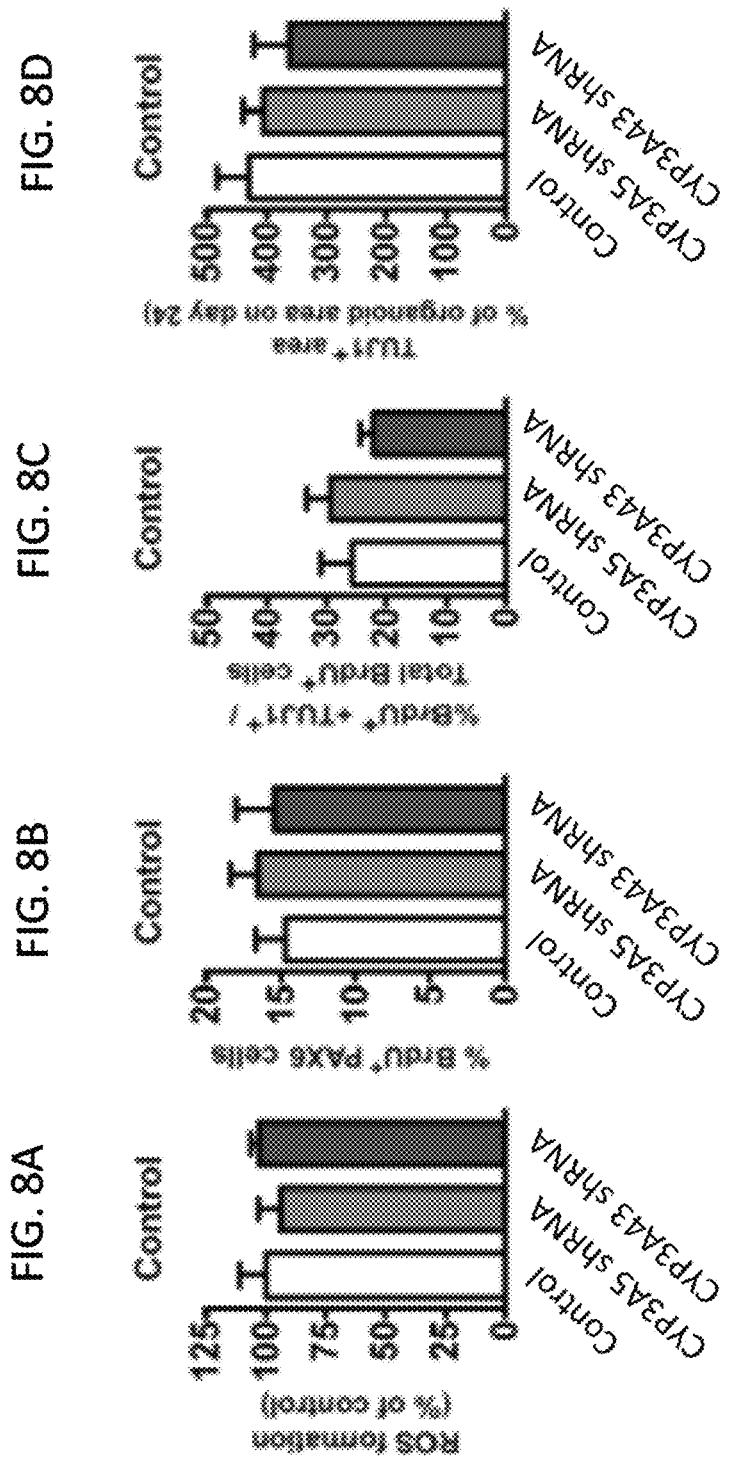

```
                            SEQUENCE LISTING

<160> NUMBER OF SEQ ID NOS: 32

<210> SEQ ID NO 1
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 1
tgtttccaag agaagttaca aattttt                                              27

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
tccactcggt gcttttgtgt                                                      20

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
actgagtccc acaaagctct gt                                                   22

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
tagccagcaa aaatgaagat tattg                                                25

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 5
ggcccacacc tctgcc                                                          16

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
```

-continued tgtcaaacgt ccaatagccc                                          20

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
tgctctcaca aacataaaac ttgct                                    25

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
cagtgggatc tgagtctctt tacaa                                    25

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
accacagtcc atgccatcac                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tccaccaccc tgttgctgta                                          20

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11 cccagcctttt actcttcct                                          19

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
gagaaggcga aatccgaag                                           19

<210> SEQ ID NO 13
<211> LENGTH: 19
<212> TYPE: DNA

<213> ORGANISM: Artificial Sequence
<220> FEATURE:
<223> OTHER INFORMATION: Synthetic oligonucleotide

<400> SEQUENCE: 13
cttcgcaagc cctcatttc                    19

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
gagaaggcga aatccgaag                    19

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
acagcgcatg atcaccag                     18

<210> SEQ ID NO 16
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 16
tttgcaaatg gattgtactt aatttt            26

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
cgccgagttg agcaagat                     18

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
ggtggtcctg catgtgct                     18

<210> SEQ ID NO 19
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (36)..(36)
<223> OTHER INFORMATION: N is inosine

<400> SEQUENCE: 19
tggcggtggg gtcctcactg tgcaaatgat aggctntc                              38

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tgtaggccct gtttctcctg                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
aacctcccat gaggctgtaa                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ggtggacagg ttcagagtcc                                                  20

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
ggcacacaca cattaacaca ctt                                              23

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 24
ggtgtgtgag agcaattctc ag                                               22

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 25
ctggatgcgc aaagttcac                                                   19

<210> SEQ ID NO 26

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 26
agcggttgta gtgaaattcc tt                                              22

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
tcatttgttg gcgactgg                                                   18

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
tgctttggac tcatcgacat                                                 20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
agcattcaag gcctcatttg                                                 20

<210> SEQ ID NO 30
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 30
gacgacacgg acactcagc                                                  19

<210> SEQ ID NO 31
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 31
aactgcattg gcatgaggtt tgctctcat                                       29

<210> SEQ ID NO 32
<211> LENGTH: 29
<212> TYPE: DNA
```

```
<213> ORGANISM: Artificial Sequence
<220> FEATURE:
<223> OTHER INFORMATION: Synthetic oligonucleotide

<400> SEQUENCE: 32
gtactggaca gagcctgaga agttctgcc                                              29
```

THREE-DIMENSIONAL MODEL OF HUMAN CORTEX

CROSS REFERENCE TO RELATED APPLICATION

This claims the benefit of U.S. Provisional Application No. 62/151,243, filed Apr. 22, 2015, which is incorporated herein by reference in its entirety.

ACKNOWLEDGMENT OF GOVERNMENT SUPPORT

This invention was made with governmental support through the National Institutes of Health. The government has certain rights in the invention.

FIELD

This invention relates to the field of methods for the in vitro production of differentiated neuronal cells from stem cells, such as the production of neocortical cells.

BACKGROUND

It has been suggested that prenatal cocaine exposure exerts its effect on neurobehavioral development through impaired frontal cortical development (Rando et al., *Biol. Psychiatry* 74:482-489, 2013; Roussotte et al., *J. Neurodev. Disord.* 4:22, 2012); however, elucidation of these effects in human subjects is fraught with difficulties related to numerous confounding variables such as multi-drug usage, nutrient intake, environmental factors (Ackerman et al., *Pediatrics* 125:554-565, 2010), and, potentially, genetic differences. Importantly, the underlying mechanisms defining the relationship between genetic factors and varying responses to cocaine are not known. It has previously been demonstrated that, in rats, prenatal cocaine exposure during the most active period of neural progenitor proliferation induces cytoarchitectural changes in the embryonic neocortex (Lee et al., *Synapse* 65:21-34, 2011). These cytoarchitectural changes are initiated by N-oxidative metabolism of cocaine and consequent oxidative ER stress signaling (Lee et al., *PLoS Med.* 5:e117, 2008). However, due to the significant differences between humans and rodents in neocorticogenesis (Rakic, *Nat. Rev. Neurosci.* 10:724-735, 2009) and CYP-mediated drug metabolism (Martignoni et al., *Expert Opin. Drug Metab. Toxicol.* 2:875-894, 2006) it has been difficult to translate these findings from the rodent model directly to human development.

SUMMARY

Disclosed herein are methods for differentiation of neuronal cells from stem cells, which in some embodiments, produce a three-dimensional model of the neocortex. In other embodiments, the disclosed methods produce a two-dimensional model of the neocortex. The methods include contacting stem cells with a set of defined media and conditions, which can produce formation of a neocortical organoid.

In some embodiments, the methods include culturing stem cells (such as embryonic stem cells or pluripotent stem cells) with at least one inhibitor of SMAD signaling and at least one inhibitor of fibroblast growth factor (FGF) signaling for a period of time to result in formation of an embryoid body. In some examples, the inhibitor of SMAD signaling is LDN193189 and/or SB431542 and the inhibitor of FGF signaling is PD0325901. The embryoid body is then cultured with at least one FGF (for example, basic FGF (bFGF)) for a period of time sufficient to produce a neuroepithelial (NE) rosette. In some embodiments, the rosette is at least about 50,000 µm². In particular examples, the rosette is isolated and cultured in suspension culture (for example, under low attachment conditions) in the presence of at least one FGF for a period of time sufficient to produce cells with dorsal cortical identity. In other examples, the rosette is isolated and cultured in adherent culture in the presence of at least one FGF for a period of time sufficient to produce cells with dorsal cortical identity. In some examples, the rosette is cultured in the presence of bFGF and FGF18. The cells with dorsal cortical identity are then cultured in the substantial absence of trophic factors for a period of time sufficient to form a neocortical organoid.

The foregoing and other features of the disclosure will become more apparent from the following detailed description, which proceeds with reference to the accompanying figures.

BRIEF DESCRIPTION OF THE DRAWINGS

FIG. 1 is a schematic diagram of an exemplary method of producing neocortical organoids.

FIG. 2A is a series of panels showing time-course analysis of gene expression for pluripotency, early germ layer, and neural markers. n=3. FIG. 2P is a series of panels showing voltage clamp recording from a cell with RMP of −53 mV. Voltage commands (upper left) and corresponding current traces (lower left) are shown with the peak sodium (upper right) and potassium (lower right) currents plotted against membrane potential. Data are shown as means±s.e.m. Cell line: H9.

FIG. 3A is a series of graphs showing time-course analysis of gene expressions for neural markers. n=3. Data are shown as means±s.e.m. FIG. 3B is a series of images of cryosections of neocortical structures immunostained for cortical markers CTIP2 or CUX1 at day 66. Scale bar, 100 μm for CTIP2/DAPI and 50 μm for CUX1/DAPI. FIG. 3C is a graph showing cumulative distribution of resting membrane potentials (n=45) in neocortical neurons generated from hPSCs at day 66. The potentials follow a Gaussian distribution with a mean of −40±17 (s.d.) mV. FIG. 3D is a graph showing distributions of the peak sodium (left) and potassium currents (right) in neocortical neurons generated from hPSCs at day 66. Each symbol represents a different cell. Means and standard deviations are shown by horizontal bars. Cell line: H9.

FIGS. 4A-4D is a series of panels showing imaging of neocortical organoids from hPSCs using CLARITY method. FIGS. 4A-4C show passively cleared neocortical organoid at day 66, using paraformaldehyde-fixed/hydrogel embedded/non-ETC (passive-clearing) methodology, before (FIG. 4A) and after (FIGS. 4B-4C) clearing (neocortical organoids indicated by arrows). FIG. 4D is a series of panels showing 3-dimensional immunohistological visualization of the intact neocortical organoid at day 66 stained for TUJ1 (green). Scale bar, 100 μm. Cell line: H9.

FIG. 5A is an image showing RT-PCR analysis of expression of CYP3A family genes at different stages of neocortical organoid differentiation. "Neocortical organoids" indicates day 44 of differentiation. FIG. 5B is a graph showing ROS formation in the neocortical organoids in presence or absence of cocaine. Neocortical organoids were treated with 3 μM cocaine for 1 h every other day from day 32 to day 44, and endogenous ROS was measured at day 44. n=6. FIG. 5C is a graph showing effects of CYP3A5 or CYP3A43 knockdown on cocaine-induced ROS generation in H9 (dashed line, in the absence of cocaine). n=6. FIG. 5D is a graph showing proliferation of PAX6$^+$ NE cells of neocortical organoids in the presence or absence of cocaine in H9. Proliferation was examined at day 45 with 1 h BrdU (10 μM) incorporation. n=5. FIG. 5E is a graph showing effects of CYP3A5 or CYP3A43 knockdown on cocaine-induced inhibition of proliferation of PAX6$^+$ NE cells in H9 (dashed line, in the absence of cocaine). n=7. FIG. 5F is graph showing neuronal differentiation in neocortical organoids in the presence or absence of cocaine in H9. Neuronal differentiation was analyzed 24 h after 1 h BrdU (10 μM) treatment from day 51 to day 52. Percentages of BrdU$^+$ cells exhibiting neuronal identity (TUJ1$^+$) are shown. n=5. FIG. 5G is a graph showing effects of CYP3A5 or CYP3A43 knockdown on cocaine-induced premature neuronal differentiation in H9 (dashed line, in the absence of cocaine). n=7, FIG. 5H is a graph showing neural tissue development in the presence or absence of cocaine in H9. TUJ1$^+$ areas in the neocortical organoids were analyzed at day 66. TUJ1$^+$ areas expressed as percentages of total organoid area on day 24 are shown. n=6. FIG. 5I is a graph showing effects of CYP3A5 or CYP3A43 knockdown on cocaine-induced inhibition of neural tissue development in H9 (dashed line, in the absence of cocaine). n=6. Data are shown as means±SEM. Unpaired two-tailed Student's t-test for H9 and H14 in FIG. 5B, and for FIGS. 5D, 5F, and 5H. One-way ANOVA followed by Tukey's compromise post-hoc test for FIGS. 5C, 5G, and 5I. Dunn's multiple comparisons test for e. *P<0.05 and **P<0.01.

FIG. 6A shows proliferation of PAX6+NE cells of neocortical organoids in the presence or absence of cocaine in H14. Proliferation was examined at day 45 with 1 h BrdU (10 μM) incorporation. n=6. FIG. 6B is a graph showing neuronal differentiation in neocortical organoids in the presence or absence of cocaine in H14. Neuronal differentiation was analyzed 24 h after 1 h BrdU (10 μM) treatment from day 51 to day 52. n=6. FIG. 6C is a graph showing neural tissue development in the presence or absence of cocaine in H14. TUJ1+ areas in the neocortical organoids were analyzed at day 66. Total TUJ1+ areas are expressed as percentages of total organoid area on day 24. n=5. Data are shown as means±SEM. Mann-Whitney U-test for FIG. 6A. Unpaired two-tailed Student's t-test for FIGS. 6B and C. *P<0.05 and **P<0.01.

FIGS. 8A-8D is a series of graphs showing the effects of CYP3A5 or CYP3A43 knockdown on development of neocortical organoids. FIG. 8A is a graph showing ROS formation in neocortical organoids (H9) at day 44. n=6. FIG. 8B is a graph showing proliferation of PAX6+NE cells of neocortical organoids (H9) at day 45 with 1 h BrdU (10 μM) incorporation. n=6. FIG. 8C is a graph showing neuronal differentiation in neocortical organoids (H9) analyzed 24 h after 1 h BrdU (10 μM) treatment from day 51 to day 52. n=6. FIG. 8D is a graph showing neural tissue development (H9) at day 66. n=6. Data are shown as means±SEM.

SEQUENCE LISTING

Figure 2A:
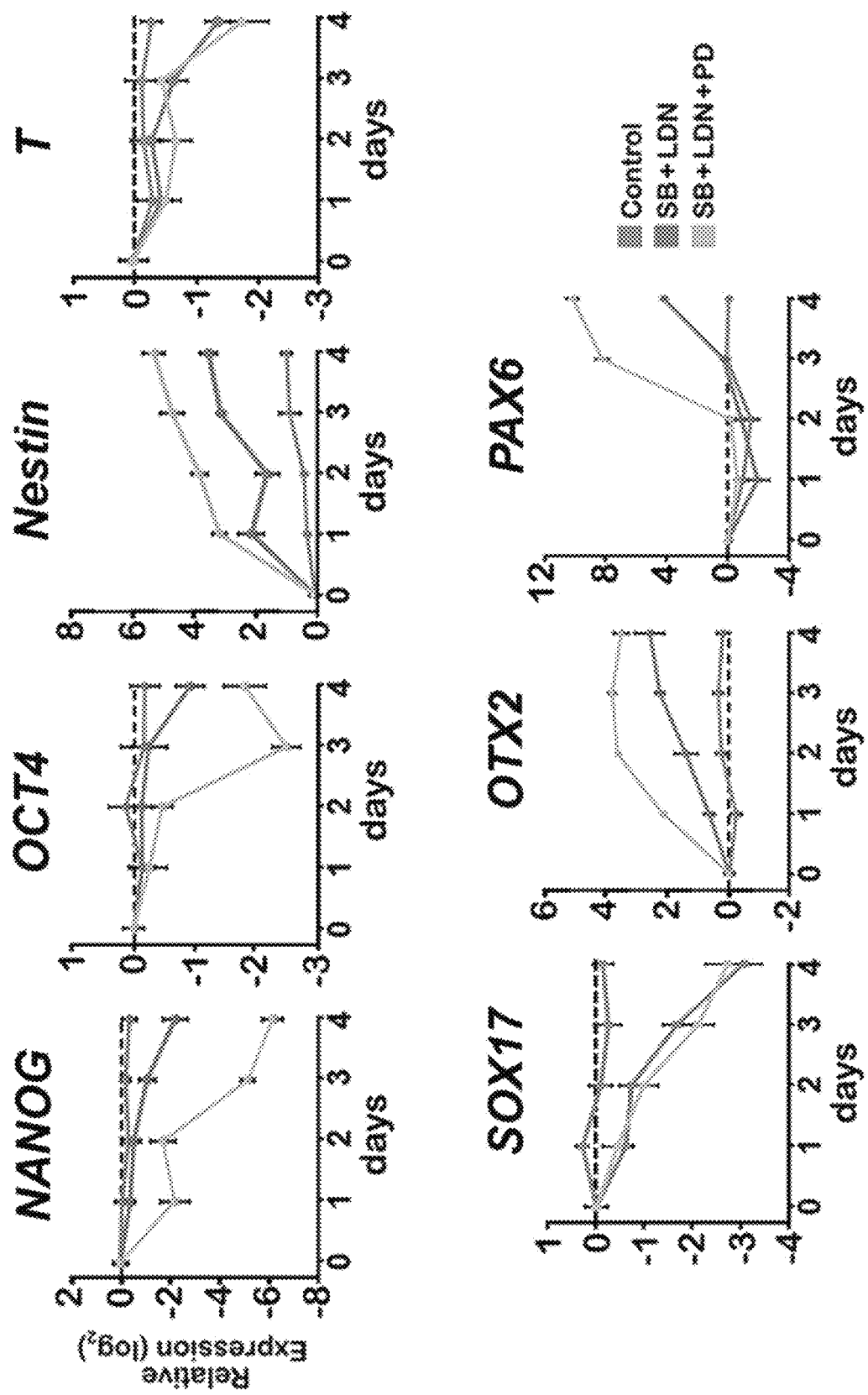
FIGS. 2A-2P are a series of panels showing neocortical organoid generation from hPSCs.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Apr. 21, 2016, and is 6651 bytes, which is incorporated by reference herein.

SEQ ID NOs: 1-30 are oligonucleotide primers.
SEQ ID NOs: 31-32 are CYP3A5 and CYP3A43 shRNAs, respectively.

DETAILED DESCRIPTION

Disclosed herein are methods of inducing neocortical organoid structures in an in vitro system. The methods utilize a protocol with defined patterning molecules and neocortical trophic factors. The methods include preserving pluripotent stem cell aggregates, which without being bound by theory, are hypothesized to retain intercellular communication (e.g., via gap junctions) and provide intrinsic cues for cellular differentiation. The methods disclosed herein overcome some of the drawbacks previous hPSC-based 3D cerebral organoid in vitro model systems (such as that described in Lancaster et al., Nature 501:373-379, 2013), including inconsistent brain regionalization, and the use of MATRIGEL® embedding, which interferes with in vitro drug treatment.

The disclosed methods include forming embryoid bodies from stem cells (for example, by culture in the presence of inhibitors of SMAD signaling and/or FGF signaling) and forming neuroepithelial (NE) rosettes, for example by culture of embryoid bodies in the presence of at least one FGF during formation of rosettes. The NE rosettes are then cultured in suspension culture with at least one FGF, followed by culture in the substantial absence of trophic factors (for example, in medium without any added trophic factors). The inventors have determined that a significant increase in rosette size occurs upon treatment with a combination of LDN193189, SB431542, and PD0325901. As disclosed herein, the size of the NE rosettes utilized in the method is important for successful cellular differentiation and formation of neocortical organoids, with smaller rosettes (e.g., less than 10,000 $\mu m^2$) being less effective for neocortical organoid differentiation and rosette size at least 50,000 $\mu m^2$ or larger was most reliable for robust neocortical organoid growth. Moreover, blockade of dual SMAD and FGF signaling significantly increased the percentage of colonies containing NE rosettes, facilitating the collecting of rosettes for subsequent organoid differentiation. Finally, the inventors determined that LDN193189, SB431542, and PD0325901 treatment during the beginning embryoid body stage, followed by supplementation with bFGF, efficiently yielded rosettes with dorsopallial identity. Without being bound by theory, it is believed that larger rosettes contribute to the development of neocortical organoids by contributing a critical mass of cellular material to interact, providing growth cues to neighboring cells. In prior methods to produce cortical structures from embryonic stem cells, this aim has been achieved by combining variable numbers of smaller rosettes, with the attendant disadvantage of resulting in a disorganized structure.

The neocortical organoids produced by the methods disclosed herein have a variety of uses, including as in vitro models for testing drugs, such as agents for treating CNS disorders, agents to counteract developmental disorders of neocortical development, or agents that may have adverse effects on cortical development. The neocortical organoids can also be used to study neuronal function in vitro.

I. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Absence: A condition in which a particular compound or component is not present. However, the term "absence" does not require an absolute lack of the indicated compound. In some examples, "absence" of a compound includes a medium wherein exogenous compounds (for example, one or more trophic factors) is not added, or medium that contains less than a particular amount of the compound (for example, less than about 25 pg/ml of the compound, such as less than about 15 pg/ml, less than about 10 pg/ml medium, less than about 5 pg/ml, or less than about 1 pg/ml). In another example, "absence" indicates that the compound cannot be detected using a standard assay, such as an immunoassay (for example ELISA or bead-based assays) or mass spectrometry.

Central Nervous System (CNS): The part of the nervous system of an animal that contains a high concentration of cell bodies and synapses and is the main site of integration of nervous activity. In higher animals, the CNS generally refers to the brain and spinal cord.

Dorsal cortical identity: Cells that have at least one characteristic of dorsal cortical neurons. In some non-limiting examples, cells with dorsal cortical identity express one or more of telencephalic transcription factor BF1, PAX6, and EMX1. In a particular example, cells with dorsal cortical identity express all of BF1, PAX6, and EMX1.

Culturing or Cell Culture: Growth or maintenance of a population of cells in a defined set of conditions (such as culture medium, extracellular matrix, temperature, and/or time of culture) in vitro. In some examples, a cell culture includes a substantially pure culture (for example, isolated embryonic stem cells or isolated induced pluripotent stem cells). In additional examples a cell culture includes a mixed culture, such as co-culture of two or more types of cells (for example a culture of embryonic stem cells with a feeder layer). In further examples, a cell culture includes cells grown in contact with an extracellular matrix (such as an extracellular matrix including poly-L-ornithine and/or laminin).

Differentiation: The process whereby relatively unspecialized cells (e.g., embryonic cells and/or stem cells) acquire specialized structural and/or functional features characteristic of mature cells. Similarly, "differentiate" refers to this process. Typically, during differentiation, cellular structure alters and tissue-specific proteins and properties appear. The term "differentiated neuronal cell" refers to cells expressing a nucleic acid or protein characteristic of the specific neuronal cell type, exhibiting synaptic vesicle release, or having an electrophysiological characteristic of a neuronal cells (e.g., sustained bursts of action potentials). A differentiated neuronal cell can be a cortical cell.

Differentiation medium: A synthetic set of culture conditions with the nutrients necessary to support the growth or survival of cells, and which allows the differentiation of cells, such as stem cells.

Embryoid bodies (EB): Stem cell aggregates generated when stem cells (for example, embryonic stem cells) are plated on a non-adhesive surface that prevents attachment and differentiation of the stem cells. Generally, embryoid bodies include an inner core of undifferentiated stem cells surrounded by primitive endoderm.

Embryonic Stem Cells (ES cells or ESC): Pluripotent cells isolated from the inner cell mass of the developing blastocyst, or the progeny of these cells. "ES cells" can be derived from any organism. ES cells can be derived from mammals, including mice, rats, rabbits, guinea pigs, goats, pigs, cows, non-human primates, and humans. In specific, non-limiting examples, the cells are human, non-human primate, or murine. Without being bound by theory, ES cells can generate a variety of the cells present in the body (bone, muscle, brain cells, etc.) provided they are exposed to conditions conducive to developing these cell types. Methods for producing murine ES cells can be found in U.S. Pat. No. 5,670,372, which is herein incorporated by reference. Methods for producing human ES cells can be found in U.S. Pat. No. 6,090,622, WO 00/70021 and WO 00/27995, which are herein incorporated by reference.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion" or "expanded." Typically, during an expansion phase, the cells do not differentiate to form mature cells.

Fibroblast growth factor or FGF: Any suitable fibroblast growth factor, derived from any animal, and functional fragments thereof. A variety of FGFs are known and include, but are not limited to, FGF1 (acidic fibroblast growth factor), FGF2 (basic fibroblast growth factor, bFGF), FGF3 (int-2), FGF4 (hst/K-FGF), FGF5, FGF6, FGF7, FGF8, FGF9, FGF18, and FGF98. "FGF" refers to a fibroblast growth factor protein such as FGF1, FGF2, FGF3, FGF4, FGF5, FGF6, FGF7, FGF8, FGF9, FGF18, FGF98, or a biologically active fragment or mutant thereof. The FGF can be from any animal species. In one embodiment, the FGF is mammalian FGF, including but not limited to, rodent, avian, canine, bovine, porcine, equine, or human. The amino acid sequences and method for making many of the FGFs are well known in the art.

FGF2 (also known as bFGF or bFGF2), and other FGFs, can be made as described in U.S. Pat. No. 5,155,214. Recombinant bFGF2, and other FGFs, can be purified to pharmaceutical quality (98% or greater purity) using the techniques described in detail in U.S. Pat. No. 4,956,455. It should be noted that human and murine bFGF, FGF18, and a variety of other FGFs, are commercially available.

An exemplary nucleic acid sequence for human bFGF can be found as GenBank Accession No. NM_002006 and an exemplary amino acid sequence can be found as GenBank Accession No. NP_001997, both incorporated by reference herein as present in GenBank on Apr. 20, 2015. An exemplary nucleic acid sequence for human FGF18 can be found as GenBank Accession No. NM_003862 and an exemplary amino acid sequence can be found as GenBank Accession No. NP_003853, both incorporated by reference herein as present in GenBank on Apr. 20, 2015.

In some embodiments, the methods disclosed herein utilize one or more inhibitors of FGF signaling. An inhibitor of FGF signaling includes molecules (such as small molecules, nucleic acids, peptides, or antibodies) that block one or more steps in the signaling cascade triggered by binding of a ligand to an FGF receptor. Thus, in some examples, an inhibitor of FGF signaling is an FGF receptor tyrosine kinase inhibitor, a STAT3 inhibitor, and Akt inhibitor, a Rac 1 inhibitor, a MEK inhibitor, or an ERK1/2 inhibitor. In one particular example, the inhibitor of FGF signaling is a MEK inhibitor, for example a MEK1 inhibitor, a MEK2 inhibitor, and/or a MEK1/2 inhibitor, such as PD0325901, PD98059, U0126, trametinib (GSK1120212), cobimetinib (XL518), binimetinib (MEK162), or selumetinib (AZD6244). Inhibitors of FGF signaling are commercially available.

Growth medium or expansion medium: A synthetic set of culture conditions with the nutrients necessary to support the growth (cell division/expansion) of a specific population of cells. In one embodiment, the cells are stem cells (for example, ES cells or EC cells). In this embodiment, the growth media is a stem cell growth medium that allows stem cells to proliferate. In another embodiment, the cells are neuronal precursor cells. In this embodiment, the expansion medium is a neuronal precursor cell expansion medium that allows neuronal precursors to proliferate.

Growth media generally include a carbon source, a nitrogen source and a buffer to maintain pH. In one embodiment, stem cell growth medium contains a minimal essential media, such as DMEM, supplemented with various nutrients to enhance stem cell growth. Additionally, the minimal essential media may be supplemented with additives such as horse, calf or fetal bovine serum.

Isolated: An "isolated" biological component (such as a nucleic acid, peptide or protein) has been substantially separated, produced apart from, or purified away from other biological components in the cell of the organism in which the component naturally occurs, for example, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. In some examples, an isolated cell includes a cell that has been substantially purified from other cell types.

Neocortical organoid: A three-dimensional structure produced in vitro that has at least some features of brain cortex in vivo. In some examples, a neocortical organoid is a self-organizing structure of differentiated cortical neurons having polarized neuroepithelia with ventricle-like cavities (or a lumen) at the center. In some examples, a neocortical organoid expresses one or more genes, including for example, one or more of BF1, PAX 6, EMX1, N-cadherin, CD133, gamma-tubulin, TBR1, TUJ1, Reelin, CTIP2, and CUX1. In some examples, a neocortical organoid expresses apical end markers (such as one or more of N-cadherin, CD133, and gamma-tubulin) localized to the center of the organoid, e.g., facing the lumen. In other examples, the neocortical organoid expresses TBR1 in TUJ1-expressing areas surrounding the dorsopallial neuroepithelia. Reelin-positive cells may be found in the most superficial layer of the TBR1$^+$ zone. The neocortical organoid may also include early cortical plate neurons (for example, expressing CTIP2) and late cortical plate neurons (for example, expressing CUX1).

Figure 2B:
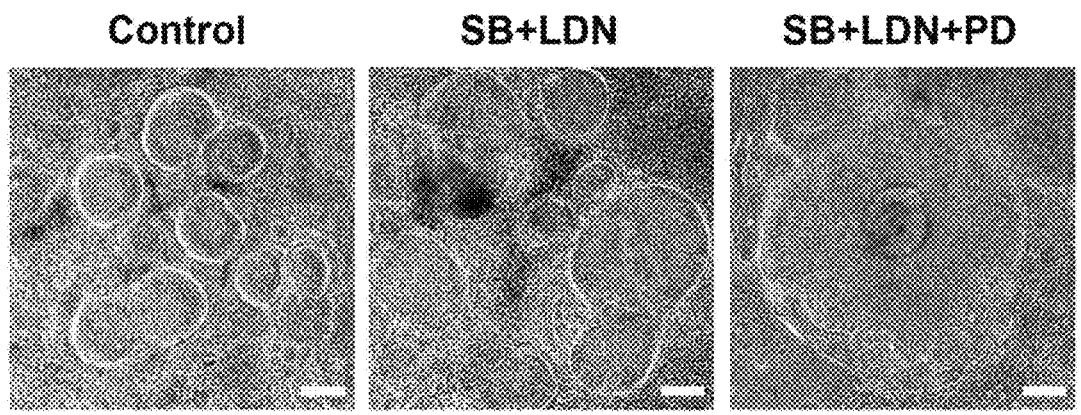
FIG. 2B is a series of phase contrast images of NE rosettes derived from hPSCs at day 16. Scale bar, 100 µm.
Figure 2C:
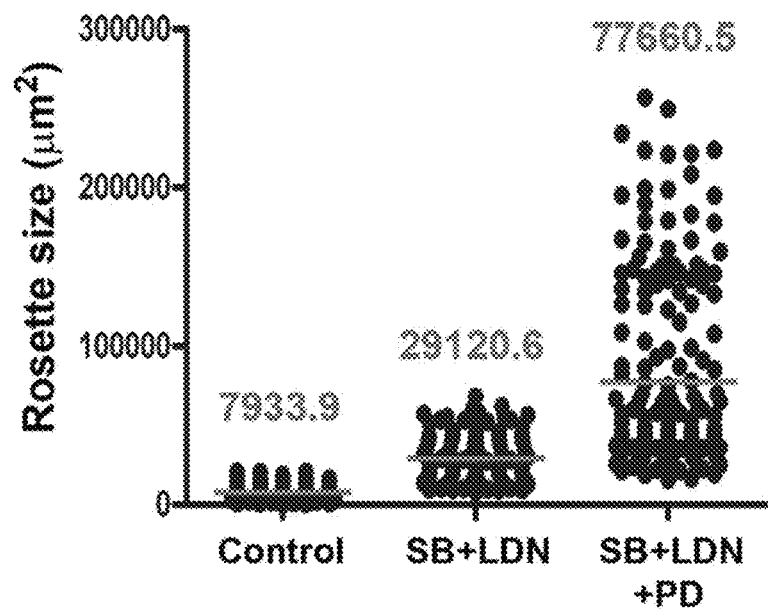
FIG. 2C is a graph showing distribution of sizes of rosettes at day 16. n=128 for control, 142 for SB+LDN, and 176 for SB+LDN+PD, from three independent experiments. Red line indicates mean.
Figure 2D:
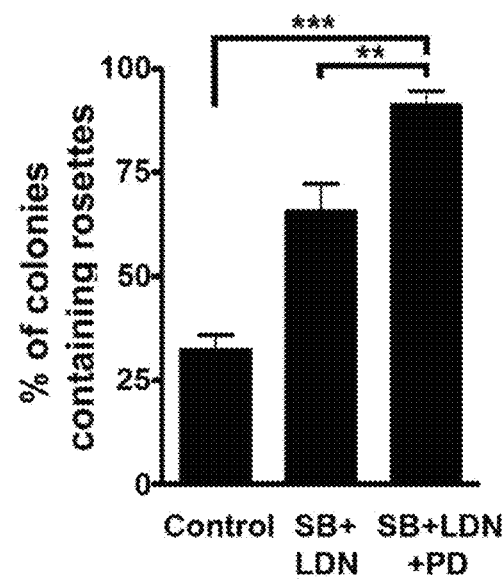
FIG. 2D is a graph showing analysis of percentages of colonies containing rosettes at day 16. n=9 independent experiments; total counted colonies: 506 for control, 573 for SB+LDN, and 490 for SB+LDN+PD. One-way ANOVA followed by Tukey's compromise post-hoc test; P<0.01 and *P<0.001.

Neuroepithelial (NE) rosette: A structure with a rosette-like shape, with cells in a flower petal-like arrangement, for example, expressing markers of neuroepithelial cells, including Nestin. An example of a NE rosette is shown in FIG. 2D. In some examples, NE rosettes produced by the methods described herein express anterior telencephalic markers (e.g., BF1) and/or dorsal forebrain markers (e.g., PAX6 and/or EMX1). In some, non-limiting examples, NE rosettes produced by the methods disclosed herein do not express (or express reduced amounts of) hindbrain/spinal cord markers (e.g., HOXB4) and/or ventral telencephalic markers (e.g., NKX2.1).

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

SMADs: SMADs are intracellular proteins that transduce extracellular signals from transforming growth factor beta (TGF-β) superfamily receptors to the nucleus. SMADs are transcription factors that activate downstream gene transcription. For example, SMAD2 and SMAD3 transduce signals from the TGF-β/activin pathway, and SMADs 1/5/9 transduce signals from the bone morphogenetic (BMP) pathway.

In some embodiments, the methods disclosed herein utilize one or more inhibitors of SMAD signaling. An inhibitor of SMAD signaling includes molecules (such as small molecules, nucleic acids, peptides, or antibodies) that block one or more steps in the signaling cascade transduced by SMADs. In some examples, an inhibitor of SMAD signaling includes a BMP inhibitor such as LDN193189, or a TGF-β receptor kinase inhibitor, such as SB431542. In some examples, dual SMAD inhibition refers to inhibition of SMAD signaling via both the TGF-β and BMP pathways (by a single molecule or two or more separate molecules). Inhibitors of SMAD signaling are commercially available.

Stem cell: A cell that can generate a fully differentiated functional cell of more than one given cell type. The role of stem cells in vivo is to replace cells that are destroyed during the normal life of an animal. Generally, stem cells (for example, embryonic stem cells) can divide without limit and are totipotent or pluripotent. After division, the stem cell may remain as a stem cell, become a precursor cell, or proceed to terminal differentiation. A pluripotent stem cell is a stem cell that can generate a fully differentiated cell of more than one given cell type, but is not totipotent.

A precursor cell is a cell that can generate a fully differentiated functional cell of at least one given cell type. Generally, precursor cells can divide. After division, a precursor cell can remain a precursor cell, or may proceed to terminal differentiation. A "neuronal stem cell" is a stem cell that can be differentiated into neurons. In one embodiment, a neuronal stem cell gives rise to all of the types of neuronal cells (e.g. dopaminergic, adrenergic, and serotonergic neurons) but does not give rise to other cells such as glial cells. A "neuronal precursor cell" is a precursor cell of the nervous system.

Synapse: Highly specialized intercellular junctions between neurons and between neurons and effector cells across which a nerve impulse is conducted (synaptically active). Generally, the nerve impulse is conducted by the release from one neuron (presynaptic neuron) of a chemical transmitter (such as dopamine or serotonin) which diffuses across the narrow intercellular space to the other neuron or effector cell (post-synaptic neuron). Generally neurotransmitters mediate their effects by interacting with specific receptors incorporated in the post-synaptic cell. "Synaptically active" refers to cells (e.g., differentiated neurons) which receive and/or transmit action potentials characteristic of mature neurons.

Trophic factor: A substance that promotes cell growth and/or, survival. Trophic factors include molecules that function as growth stimulators (mitogens), molecules that function as growth inhibitors (e.g. negative growth factors), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, GenBank Accession numbers, and other references mentioned herein are incorporated by reference in their entirety for all purposes. In case of conflict, the present specification, including explanations of terms, will control. In addition, the materials, methods, and examples are illustrative only and not intended to be limiting.

II. Overview of Several Embodiments

Disclosed herein are methods for differentiation of neuronal cells from stem cells, which in some embodiments produce a three-dimensional model of the neocortex (referred to herein as a "neocortical organoid"). The methods include contacting stem cells with a set of defined media and conditions, which can produce formation of a neocortical organoid.

In some embodiments, the methods include culturing stem cells (such as embryonic stem cells or pluripotent stem cells) with at least one inhibitor of SMAD signaling and at least one inhibitor of fibroblast growth factor (FGF) signaling for a period of time to result in formation of an embryoid body. The embryoid body is then cultured with at least one FGF for a period of time sufficient to produce a neuroepithelial (NE) rosette. The rosette is then isolated and cultured in suspension culture (for example, under low attachment conditions) in the presence of at least one FGF for a period of time sufficient to produce cells with dorsal cortical identity and those cells are then cultured in the substantial absence of trophic factors for a period of time sufficient to form a three-dimensional neocortical organoid.

In other embodiments, the methods include culturing stem cells (such as embryonic stem cells or pluripotent stem cells) with at least one inhibitor of SMAD signaling and at least one inhibitor of fibroblast growth factor (FGF) signaling for a period of time to result in formation of an embryoid body. The embryoid body is then cultured with at least one FGF for a period of time sufficient to produce a neuroepithelial (NE) rosette. The rosette is then isolated and cultured under adherent conditions (such as on a plate or dish coated with laminin, poly-L-ornithine, poly-D-lysine, poly-L-lysine, poly-L-ornithine, laminin, MATRIGEL™ (BD Biosciences, Franklin Lakes, N.J.), collagen, fibronectin, fibrin, or a combination of two or more thereof) in the presence of at least one FGF for a period of time sufficient to produce cells with dorsal cortical identity and those cells are then cultured in the substantial absence of trophic factors for a period of time sufficient to form a two-dimensional neocortical organoid. In particular examples, the rosette is cultured on laminin-coated plates or poly-L-ornithine/laminin-coated plates.

In some embodiments, stem cells (such as human embryonic stem cells) are cultured under conditions to form embryoid bodies (EBs). In some examples, the conditions include culture of hESCs with at least one inhibitor of SMAD signaling (such as two or more inhibitors of SMAD signaling) and at least one inhibitor of FGF signaling during at least the first portion of EB formation. In some examples, the ESCs are cultured with media including the at least one inhibitor of SMAD signaling and at least one inhibitor of FGF signaling for about 1-6 days (such as about 1-3, 2-4, or 3-6 days, or about 1, 2, 3, 4, 5, or 6 days). In a particular example, the inhibitors are included in the medium for the first four days of the EB phase (see, e.g., FIG. 1). In some examples, about 0.01-100 µM (such as about 0.1-10 µM, about 0.05-1 µM, about 10-100 µM, or about 1-10 µM) of the at least one inhibitor of SMAD signaling is included in the medium. For example, about 0.01-1 µM (such as about 0.05-1 µM, about 0.1-0.5 µM, or about 0.1 µM) of an inhibitor of SMAD signaling such as LDN193189 is included and/or about 1-100 µM (such as about 1-50 µM, about 5-25 µM, about 1-10 µM, or about 10 µM) of an inhibitor of SMAD signaling such as SB431542 is included. Additional SMAD inhibitors can also be used, for example, one or more of dorsomorphin, LDN-193189, A83-01, and/or noggin.

In other examples, about 0.1-100 µM (such as about 1-100 µM, about 0.5-50 µM, about 1-10 µM, or about 25-50 µM) of the at least one inhibitor of FGF signaling is included in the medium. For example, about 0.1-10 µM (such as about 0.5-5 µM, about 1-5 µM, about 0.1-2 µM or about 1 µM) of an inhibitor of FGF signaling (for example, a MEK inhibitor) such as PD0325901 is included. Additional FGF signaling inhibitors, such as additional MEK inhibitors (for example a MEK1 inhibitor, a MEK2 inhibitor, and/or a MEK1/2 inhibitor) can be used, for example, one or more of PD98059, U0126, trametinib (GSK1120212), cobimetinib (XL518), binimetinib (MEK162), and selumetinib (AZD6244).

In a particular example, the at least one inhibitor of SMAD signaling is 0.1 µM LDN193189 and 10 µM SB431542 and the inhibitor of FGF signaling is 1 µM PD0325901.

The EBs are then cultured in the presence of at least one FGF under conditions sufficient to produce formation of NE rosettes. The culture can be continued until NE rosettes of a desired size are formed, for example, rosettes of at least about 10,000 µm² (such as at least 20,000, 25,000, 30,000, 40,000, 50,000, 100,000, 200,000, 300,000 µm², or more). In some examples, the rosettes are about 10,000-500,000 µm² (such as about 20,000-300,000 µm², 50,000-250,000 µm², about 25,000-100,000 µm², or about 100,000-300,000 µm²). In a particular example, the EBs are cultured with the FGF until rosettes of at least about 50,000 µm² are formed. In some examples, the EBs are cultured with the FGF for about 2-28 days (such as about 5-21 days, about 7-28 days, about 10-16 days, or about 12 days. In particular examples, the FGF is bFGF. The bFGF is included in the medium at a concentration of about 5-50 ng/ml (such as about 5-25 ng/ml, about 10-40 ng/ml, about 25-50 ng/ml, about 10-25 ng/ml, or about 15-25 ng/ml). In one example, bFGF is included in the medium at about 20 ng/ml.

Once rosettes of the desired size are produced, individual rosettes are picked and are maintained in suspension culture (for example, in low-attachment culture vessels) or in adherent culture (for example, on a plate coated with laminin or poly-L-ornithine/laminin) in the presence of at least one FGF under conditions sufficient to produce cells with dorsal cortical identity. The rosette is cultured in the presence of the at least one FGF for about 1-10 days (such as about 1-5 days, about 5-10 days, about 7-9 days, or about 8 days). In some examples, the rosette is cultured in the presence of bFGF (for example, about 5-25 ng/ml, about 10-40 ng/ml, about 25-50 ng/ml, about 10-25 ng/ml, or 20 ng/ml) and FGF18 (for example, about 5-25 ng/ml, about 10-40 ng/ml, about 25-50 ng/ml, about 10-25 ng/ml, or 20 ng/ml). In some non-limiting examples, cells with dorsal cortical identity express at least one of telencephalic transcription factor BF1, and/or the dorsal forebrain markers PAX6 and EMX1.

The cells with dorsal cortical identity are then cultured in medium in the substantial absence of exogenous trophic factors for development of the neocortical organoid structure and cell differentiation. In some examples, the medium does not include any added (exogenous) trophic factors (such as no added growth factors, such as no added FGF). In other examples the medium may contain less than about 25 pg/ml of the compound, such as less than about 15 pg/ml, less than about 10 pg/ml medium, less than about 5 pg/ml, or less than about 1 pg/ml of exogenous trophic factors. However, the medium may contain trophic factors that are produced and secreted by the cells during the period of culture. In some examples the cells are cultured in the substantial absence of exogenous trophic factors to about 2-12 weeks (such as about 3-10 weeks, about 2-8 weeks, about 3-6 weeks, or about 4-7 weeks). During this time period, the cells form three-dimensional structures that exhibit characteristics of cortical tissue, and are referred to as neocortical organoids.

III. Stem Cells

A stem cell is a cell that can generate a partially or fully differentiated functional cell of more than one given cell type. Stem cells include embryonic stem (ES) cells (for example, primate ES cells, such as human ES cells), embryonal carcinoma (EC) cells (for example, human EC cells), neuronal stem cells.

Embryonic stem cells can proliferate indefinitely in an undifferentiated state. Furthermore, ES cells are totipotent cells, meaning that they can generate all of the cells present in the body (bone, muscle, brain cells, etc.). ES cells have been isolated from the inner cell mass (ICM) of the developing murine blastocyst (Evans et al., *Nature* 292:154-156, 1981; Martin et al., *Proc. Natl. Acad. Sci.* 78:7634-7636, 1981; Robertson et al., *Nature* 323:445-448, 1986). Additionally, human cells with ES properties have been isolated from the inner blastocyst cell mass (Thomson et al., *Science* 282:1145-1147, 1998) and developing germ cells (Shamblott et al., *Proc. Natl. Acad. Sci. USA* 95:13726-13731, 1998), and human and non-human primate embryonic stem cells have been produced (see U.S. Pat. No. 6,200,806, which is incorporated by reference herein).

ES cell lines exist and can be used in the methods disclosed herein. Any human or non-human primate ES cell can be utilized with the methods disclosed herein (see U.S. Pat. No. 6,200,806, which is incorporated by reference in its entirety). In some examples, the methods described herein utilize previously derived hES cell lines. One cell line suitable for differentiation to cortical neurons by the disclosed methods is the BG01 cell line and derivatives of the BG01 cell line, such as BG01V, BG01V2, BG02, and BG03 cell lines (BresaGen; Athens, Ga.). In some examples, hES cell lines include ES04, CT2, H1, H7, H9, H14, hES1, SNUhES1, SNUhES3, SNUhES16, SA002, HE3, HSF6, EB5, CCE, and derivatives of these cell lines. One of skill in the art can select additional hES cell lines that can be used with the methods described herein. In particular, non-limiting examples, the hES cells include H1, H9, H14, or CT2 cell lines.

In other examples, mouse ES cells may also be utilized with the methods described herein. Mouse embryonic stem cells (mESCs) are pluripotent cells derived from the inner cell mass of day 3.5 blastocysts. They can be maintained in vitro for extended periods without loss of their capacity to contribute to all cell lineages when reimplanted back into a blastocyst. mESCs can also be differentiated into various cell types, including neuronal cells, in vitro. Methods of producing mESCs are well known to one of skill in the art (see, e.g., *Manipulating the Mouse Embryo A Laboratory Manual*, Second Edition, Cold Spring Harbor Laboratory Press (1994)). Mouse ES cell lines are well known to one of skill in the art. Exemplary mESCs include, but are not limited to, R1, E14.1, and B5 cell lines. One of skill in the art can select additional mES cell lines that can be used with the methods described herein to produce neuronal cells.

In additional examples, the methods described herein may be utilized with induced pluripotent stem (iPS) cells. These cells are pluripotent cells that have been reprogrammed to an embryonic-like state; iPS cells have been generated from mouse embryonic and adult fibroblasts; human fetal, newborn, and adult fibroblasts; and primate (rhesus macaque) adult fibroblasts. See e.g., Takahashi and Yamanaka, *Cell* 126:663-676, 2006; Okita et al., *Nature* 448:313-317, 2007; Wernig et al., *Nature* 448:318-324, 2007; Yu et al., *Science* 318:1917-1920, 2007; Takahashi et al., *Cell* 131:861-872, 2007; Liu et al., *Cell Stem Cell* 3:587-590, 2008. iPS cells are similar to ESCs in that they are capable of differentiation into multiple tissue types (including neurons and cardiomyocytes), formation of teratomas and embryoid bodies, and germline competency. Methods for producing iPS cells (for example, mouse or human iPS cells) are known in the art. See, e.g., Takahashi and Yamanaka, *Cell* 126:663-676, 2006; Yu et al. *Science* 318:1917-1920, 2007; Takahashi et al., *Cell* 131:861-872, 2007; Liu et al., *Cell Stem Cell* 3:587-590, 2008. Exemplary iPS cell lines include iPS (IMR90), iPS(Foreskin), iPS-DF19-9, iPS-DF4-3, and iPS-DF6-9 cell lines. iPS cell lines are available, for example, from the WiCell International Stem Cell Bank (Madison, Wis.). In particular non-limiting examples, the iPS cells include NIR-i5 or NIH-i9 cell lines.

IV. Characterization of Differentiated Cells

The neuronal cells and three-dimensional structures (e.g., neocortical organoids) resulting from the methods described herein can be characterized by methods known in the art, including assessing cell morphology, gene expression, cytoarchitecture, and/or cellular activity. In some examples, cells produced by differentiation of stem cells using the methods described herein are neuronal cells, such as cortical neuronal cells.

Neuronal cells can be identified by expression of neuronal markers, including, but not limited to, microtubule-associated protein-2 (MAP-2), Noggin, nestin, β-III tubulin, neurofilament proteins (for example, neurofilament light, medium, or heavy proteins), synapsin, synaptophysin, and growth-associated protein 43. Other suitable neuronal markers can be selected by one of skill in the art.

Cortical neuronal cells can be identified by expression of cortical neuron markers, including, but not limited to Reelin, TBR1, SATB2, CUX1, CTIP2, and/or TUJ1. Other suitable markers can be selected by one of skill in the art.

Methods of detecting expression of particular markers in a cell or cell population are well known in the art. In some examples, gene expression is assessed by measuring the amount of a nucleic acid (such as mRNA or cDNA) present in a sample, such as a differentiated stem cell. Methods of detecting a target nucleic acid molecule (such as RNA or DNA, for example mRNA or cDNA) in a sample are well known in the art. For example, nucleic acid amplification methods (with the appropriate probes and primers), as well as nucleic acid arrays (containing the appropriate probes), can be used. For example, the level of gene expression can be determined or even quantified utilizing methods well known in the art, such as Northern blots, RNase protection assays, nucleic acid arrays, reverse transcription-PCR, quantitative PCR (such as quantitative real-time PCR or Taq-Man® assays), dot blot assays, in-situ hybridization, or combinations thereof. Gene expression can also be assessed by determining the amount of a protein present in a sample, such as a differentiated stem cell. Methods of detecting a protein in a sample are well known in the art. For example, immunoassays (for example, Western blotting or ELISA) and immunocytology (for example, immunohistochemistry or flow cytometry) methods can be used.

In additional examples, cells or organoids produced by the methods described herein are identified by assessing cellular activity, for example by electrophysiology. Electrophysiological methods are well known in the art and include voltage clamp recording and patch clamp recording. In some examples, the neocortical organoids exhibit action potentials under current clamp conditions. In other examples, the neocortical organoids exhibit large voltage-gated sodium currents and/or delayed rectifier potassium currents.

The disclosure is illustrated by the following non-limiting examples:

Example 1

Formation of Neocortical Organoid Model

This example describes formation of a neocortical organoid model using human pluripotent stem cells.
Methods
Hpsc Culture:
hESC lines H1 (P46-50), H9 (P49-61), and H14 (P52-60), all from WiCell Research Institute, CT2 (P91-98, provided by University of Connecticut Stem Cell Core), and hiPSC lines NIH-i5 (P33-35) and NIH-i7 (P34-38), both provided by NIH Stem Cell Unit were employed for the 3D neocortical organoid differentiation protocol with similar results. hPSCs were propagated in feeder-dependent culture, using irradiated mouse embryonic fibroblasts (MEFs, Global Stem). hPSCs were cultured in hPSC medium, containing DMEM/F12 with 20% Knockout Serum Replacement (KSR), 2 mM L-Glutamine, Pen/Strep (50 U/ml and 50 μg/ml, respectively), 2 mM nonessential amino acids, 0.1 mM β-mercaptoethanol, and 4 ng/ml bFGF (all from Invitrogen). Colonies were passaged using 1 mg/ml Collagenase Type IV (Invitrogen) every 5 days (1:3 split ratio).

3D Neocortical Organoid Differentiation:

hPSCs were differentiated to neocortical organoids as shown schematically in FIG. 1. Undifferentiated hPSC colonies were picked up from feeder-dependent culture using 1 mg/ml Collagenase Type IV for 30 min. hPSC aggregates were preserved, allowing EB formation (Day 0). EBs were grown, floating, in hPSC medium without bFGF but including 10 μM SB431542 (Tocris), 0.1 μM LDN193189 (Stemgent), and 1 μM PD0325901 (Axon Medchem) for 4 days. The EBs were then transferred to neural media containing DMEM/F-12 (2:1) with N2 supplement, 0.1 mM non-essential amino acids, and 2 μg/ml heparin, supplemented with 20 ng/ml bFGF from days 4 to 6. Colonies were then grown in adherent culture, on laminin-coated plates, in the same media from days 6 to 16. On day 16, dorsal cortical rosettes ranging from 250 to 500 μm in diameter (~50,000 to 200,000 μm$^2$) were isolated by manual dissection and primed in suspended culture with 20 ng/ml bFGF and 20 ng/ml FGF18 for 8 days before being switched to neuronal differentiation media, containing neurobasal medium, B27 supplement, 0.1 mM non-essential amino acids, 0.5 mM L-Glutamine, and 2 μg/ml heparin for six weeks in suspension conditions to generate self-organized neocortical organoids.

Immunocytochemistry, Cell Counting, and TUJ1+ Neocortical Area Analysis:

Adherent cells in culture were fixed with 4% PFA for 10 min, followed by PBS wash. Neocortical organoids embedded in collagen gel were immersed in 4% PFA for 20 min and cryoprotected in 20% sucrose in PBS for 20 min. Cryostat sections (10 μm) were thaw-mounted onto gelatin-subbed slides. Cells and tissue sections were blocked with 0.2% Triton X-100 in PBS supplemented with 5% BSA and 10% goat serum. Cells were then incubated with primary antibodies in 0.2% Triton X-100 in PBS with 5% BSA and 5% goat serum: rabbit anti-BF1 (1:100; Abcam), rat anti-CD133 (1:100; Millipore), rat anti-CTIP2 (1:50; Abcam), rabbit anti-CUX1 (1:100; Santa Cruz Biotechnology), rabbit anti-EMX1 (1:50; Sigma), mouse anti-gamma-tubulin (1:500; Sigma), rat anti-HOXB4 (1:50; DSHB), mouse anti-Ki67 (1:100; BD Biosciences), rabbit anti-N-cadherin (1:100; Abcam), mouse anti-Nestin (1:50; R&D Systems), mouse anti-NKX2.1 (1:200; Chemicon), mouse anti-PAX6 (1:50; DSHB), rabbit anti-PAX6 (1:300; Covance), rabbit anti-PH3 (1:500; Cell Signaling Technology), mouse anti-Reelin (1:200; Millipore), rabbit anti-TBR1 (1:1000; Abcam), and mouse anti-TUJ1 (1:2,000; Promega). Corresponding fluorescent-labeled secondary antibodies were used (Alexa-Fluor 488 for green, Alexa-Fluor 555 for red; R&D Systems). Images were captured using a Carl Zeiss Axiovert 200M microscope. For TUJ1+ neocortical area analysis, organoids were cultured in individual wells of 96-well plates at day 24. TUJ1+ neocortical areas were calculated by normalization of TUJ1+ areas in the neocortical organoids at day 66 (using only sections from the center of each organoid) to organoid size at day 24.

Electrophysiology:

Neocortical organoids suspended by means of a suction pipette (ca. 50 μm i.d.) were recorded at 22° C. in a bathing medium formulated to match the Neurobasal growth medium. The composition was (mM): NaCl, 83; KCl, 5.3; $CaCl_2$, 1.8; $MgCl_2$, 0.81, HEPES (hemi-sodium), 11.0; glucose, 25; pH 7.4, 220 mOsm. The cells were recorded using an Axopatch 200 B amplifier with capacitance and access resistance compensation and using conventional patch pipettes filled with an intracellular saline composed of (mM): $KMeSO_4$, 88; $MgCl_2$, 2; $CaCl_2$, 1, HEPES-KOH, 10; EGTA, 11; pH 7.2; 210 mOsm.

Results

Inhibition of dual SMAD signaling has been shown to dramatically enhance neural conversion of hPSCs (Chambers et al., *Nat. Biotechnol.* 27:275-280 2009). In addition, FGF signaling at an early stage of hPSC differentiation has been shown to block neural differentiation (Greber et al., *EMBO J.* 30:4874-4884, 2011). Here we tested whether combined blockade of both dual SMAD signaling, using LDN193189 and SB431542, and FGF signaling, using PD0325901, would result in efficient neuroectoderm conversion from embryoid bodies, and generate NE rosettes of appropriate size for neocortical organoid differentiation. Combined treatment with dual SMAD and FGF inhibitors accelerated loss of pluripotency, through rapid down-regulation of NANOG and OCT4, and increased the efficacy of neuroectodermal differentiation though up-regulation of Nestin. Additionally, blocking both dual SMAD and FGF signaling suppressed mesodermal and endodermal fates, through down-regulation of T and SOXI, but showed no significant differences when compared to blockade of dual SMAD signaling alone (FIG. 2A). Without being bound by theory, it is hypothesized that effects on relative neuroectodermal fate were due to dual SMAD inhibition and that FGF inhibition increased departure of the cells from pluripotency.

Figure 3A:
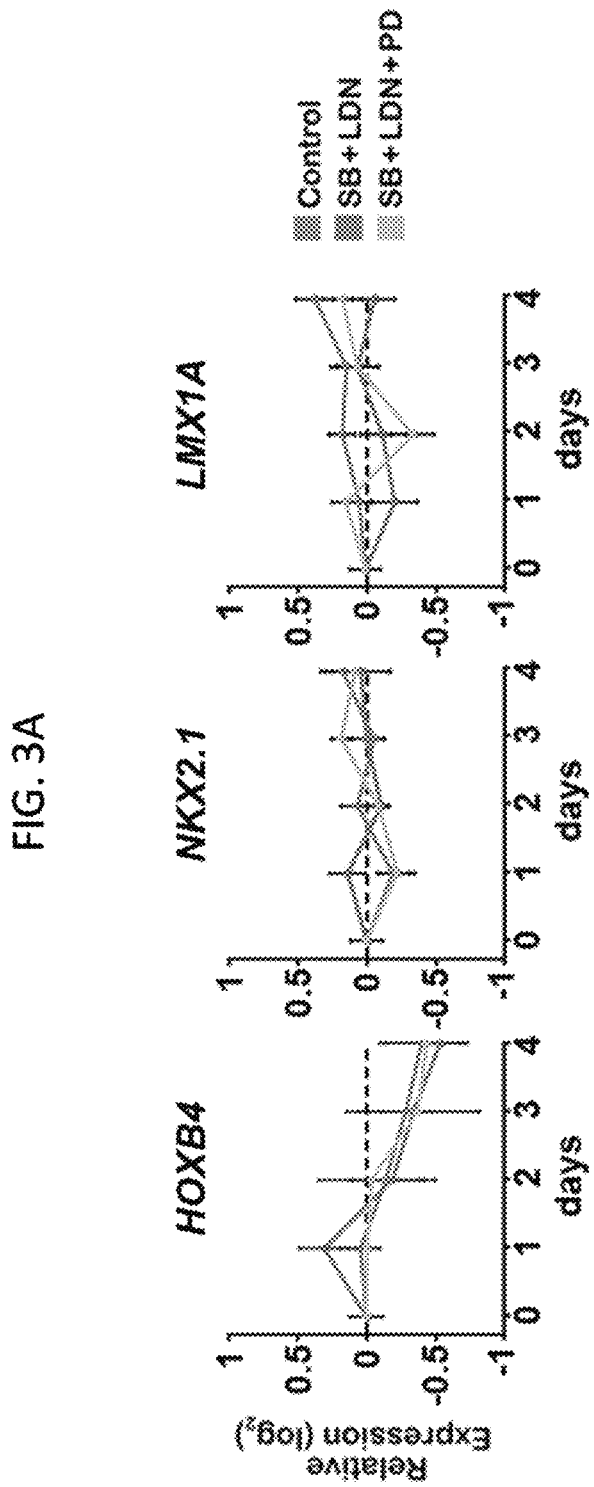
FIGS. 3A-3D is a series of panels showing characterization of neocortical organoid differentiation with Dual-SMAD and FGF inhibition.

The combined action of dual SMAD and FGF inhibition on exit from self-renewal may be related to regulation of NANOG expression by TGFbeta/activin and FGF. Suppression of TGFbeta/activin and FGF-induced pluripotency enhanced the differentiation of hPSCs toward the neuroectodermal lineage. Inhibition of dual SMAD and FGF signaling also rapidly induced expression of OTX2, an anterior telencephalic transcription factor, prior to the expression of dorsal forebrain marker PAX6 (FIG. 2A). Moreover, PAX6 induction started at day 3, when NANOG and OCT4 were nearly fully down-regulated (FIG. 2A). These results are consistent with previous findings that OTX2 acts as positive regulator, while NANOG and OCT4 act as negative regulators, of PAX6 (Greber et al., *EMBO J.* 30:4874-4884, 2011). In addition, blockade of dual SMAD and FGF signaling did not change the expression of alternative brain region markers, such as hindbrain/spinal cord marker HOXB4, ventral telencephalic marker NKX2.1, and midbrain marker LMX1A (FIG. 3A). Taken together, these data suggest that LDN193189, SB431542, and PD0325901 have effects that in combination achieve efficient neocortical neuroectodermal conversion from hPSCs.

Figure 2E:
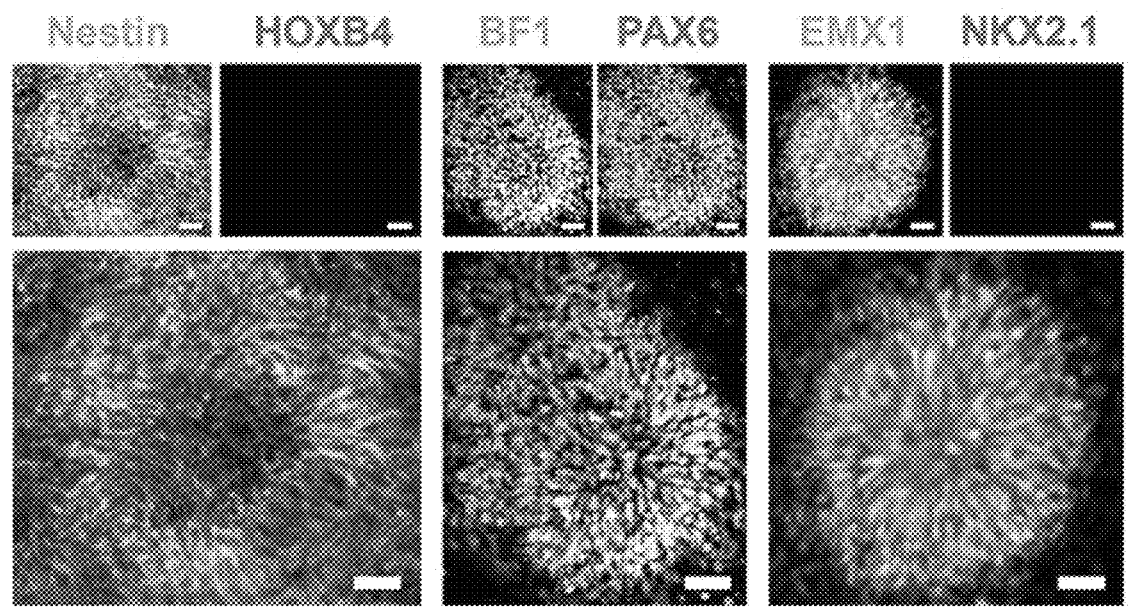
FIG. 2E is a series of images showing neocortical NE generated from hPSCs. Expression of Nestin/HOXB4, BF1/PAX6, and EMX1/NKX2.1 by immunocytochemistry at day 16. Scale bar, 50 µm.

The neocortical trophic factor, bFGF, which is known to play a role in establishing the dorsal NE of the anterior neocortex (Raballo et al., *J. Neurosci.* 20:5012-5023, 2000), was used to supplement the conversion from embryoid bodies to NE cells. The effect of dual SMAD and FGF pathway inhibition on NE rosettes was characterized at day 16. A significant increase in rosette size was observed upon treatment with LDN193189, SB431542, and PD0325901 (a 9.8-fold increase vs control; a 2.7-fold increase vs LDN193189 and SB431542) (FIGS. 2B and 2C). Additional experiments showed that a rosette size at least 50,000 μm$^2$ or larger was most reliable for robust neocortical organoid growth. Moreover, blockade of dual SMAD and FGF signaling significantly increased the percentage of colonies containing NE rosettes, facilitating the collecting of rosettes for subsequent organoid differentiation (FIG. 2D). Importantly, Nestin$^+$ NE rosettes with dual SMAD and FGF pathway inhibition expressed the anterior telencephalic transcription factors BF1, and the dorsal forebrain markers and PAX6 and EMX1 (FIG. 2E). Conversely, these rosettes did not express the hindbrain/spinal cord marker HOXB4 or the ventral telencephalic marker NKX2.1 (FIG. 2E). Therefore, LDN193189, SB431542, and PD0325901 treatment during the beginning embryoid body stage, followed by supplementation with bFGF, efficiently yielded rosettes of appropriate size with dorsopallial identity.

On day 16 dorsopallial NE rosettes were manually picked up, maintained in suspension culture, and primed with bFGF, which has been shown to maintain the proliferative NE pool (Israsena et al., *Dev. Biol.* 268:220-231, 2004), and with FGF18, which is involved in neocortical patterning and development (Hasegawa et al., *J. Neurosci.* 24:8711-8719, 2004) for 8 days. All trophic factors were then removed from the cultures during the final six weeks of differentiation to allow for self-organized neocortical organoid formation.

Figure 2F:
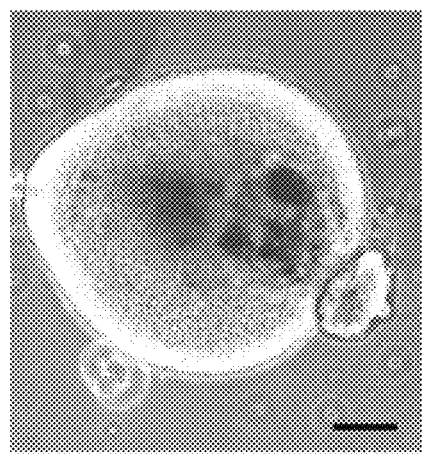
FIG. 2F is a phase-contrast image of a floating neocortical organoid derived from hPSCs at day 38. Scale bar, 100 µm.
Figure 2G:
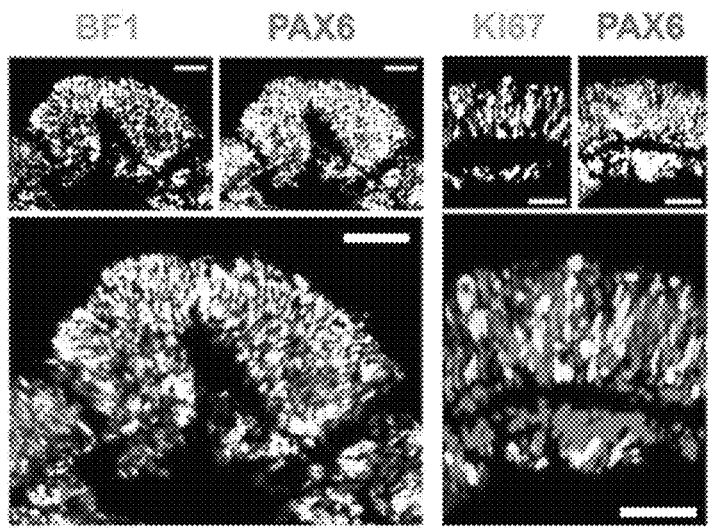
FIG. 2G is a series of images of cryosections of neocortical structures immunostained for BF1/PAX6 and Ki67/PAX6.
Figure 2H:
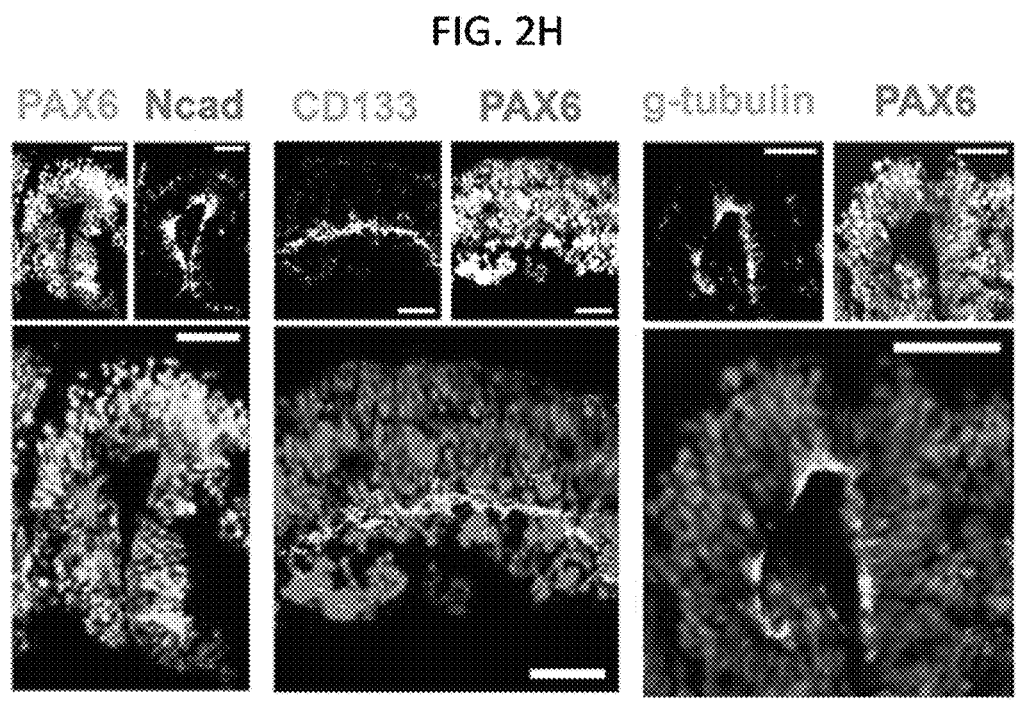
FIG. 2H is a series of images of cryosections of neocortical structures immunostained for PAX6/Ncad, CD133/PAX6, and g-tubulin/PAX6.
Figure 2I:
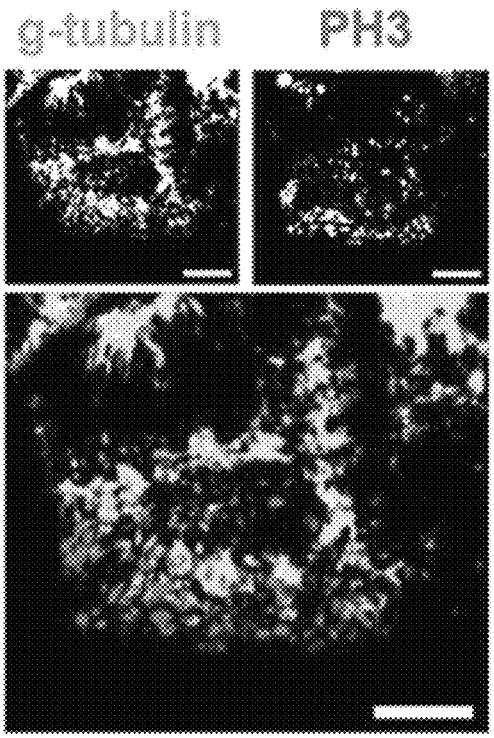
FIG. 2I is a series of images of cryosections of neocortical structures immunostained for g-tubulin/PH3.
Figure 2J:
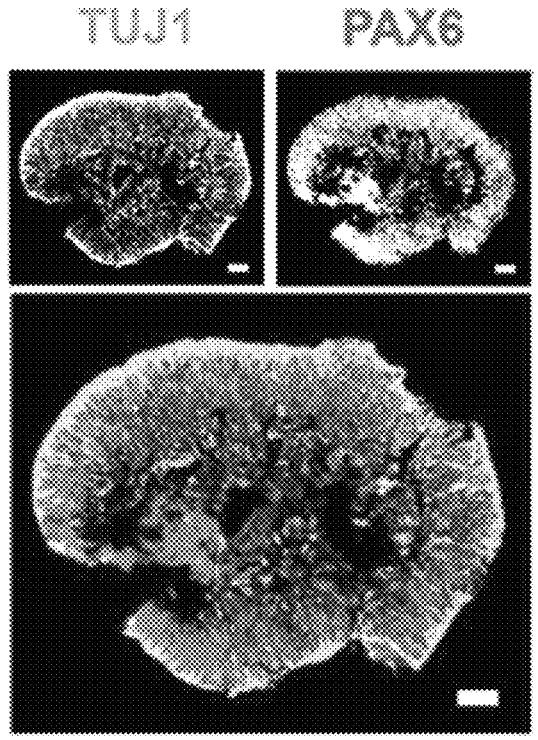
FIG. 2J is a series of images of cryosections of neocortical structures immunostained for TUJ1/PAX6.
Figure 2K:
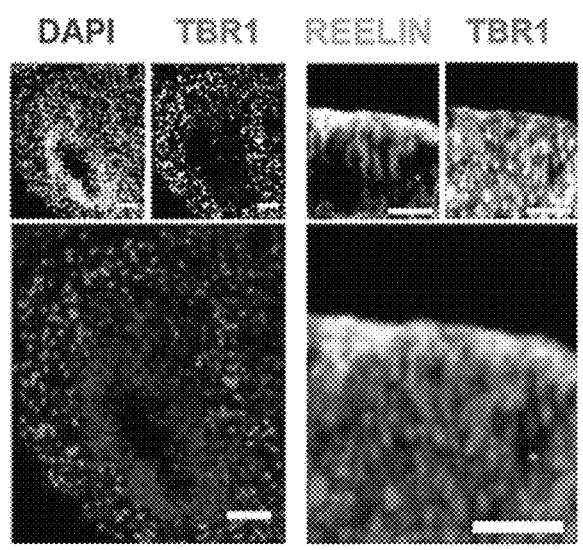
FIG. 2K is a series of images of cryosections of neocortical structures immunostained for DAPI/TBR1 and REELIN/TBR1 at day 38.
Figure 2L:
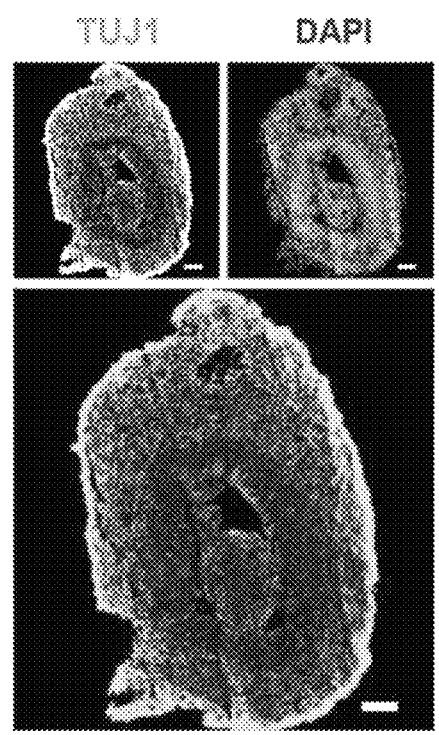
FIG. 2L is a series of images of cryosections of neocortical structures immunostained for TUJ1/DAPI at day 66. Scale bar, 50 µm for FIGS. 2H-2L. Scale bar, 25 µm for REELIN/TBR1 in FIG. 2K.
Figure 2M:
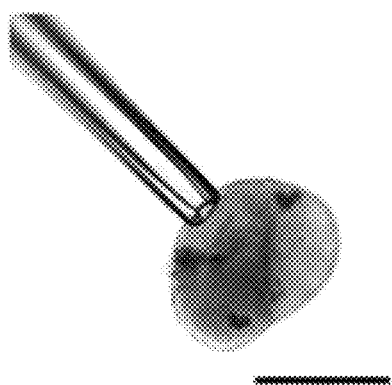
FIG. 2M is an image showing a patch pipette approaching a cell (indicated by arrow) on the organoid surface. Scale bar, 25 µm.
Figure 2N:
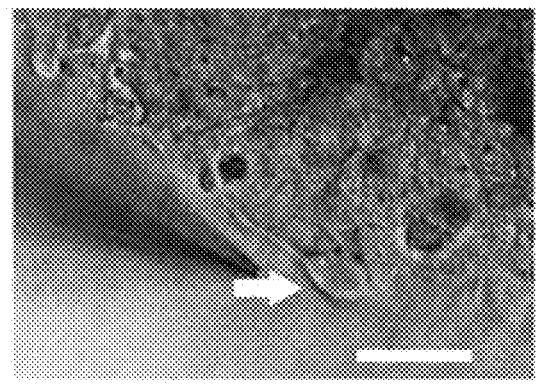
FIG. 2N is an image showing a typical neocortical organoid at day 66 held with minimal suction by a suction pipette. Scale bar, 300 µm.
Figure 2O:
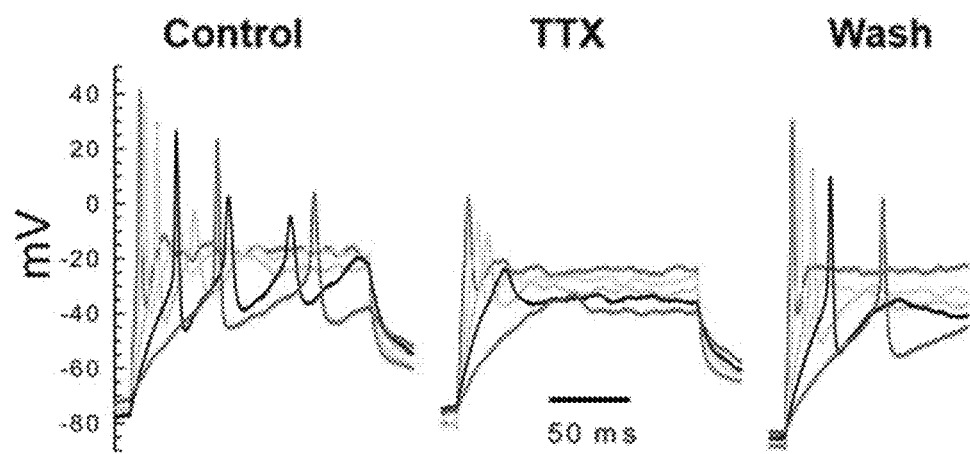
FIG. 2O is a series of voltage traces recorded in current clamp mode while injecting current in increasing increments. The strong action potentials recorded under control condition were blocked by tetrodotoxin, and recovered upon washing.
Figure 2P:
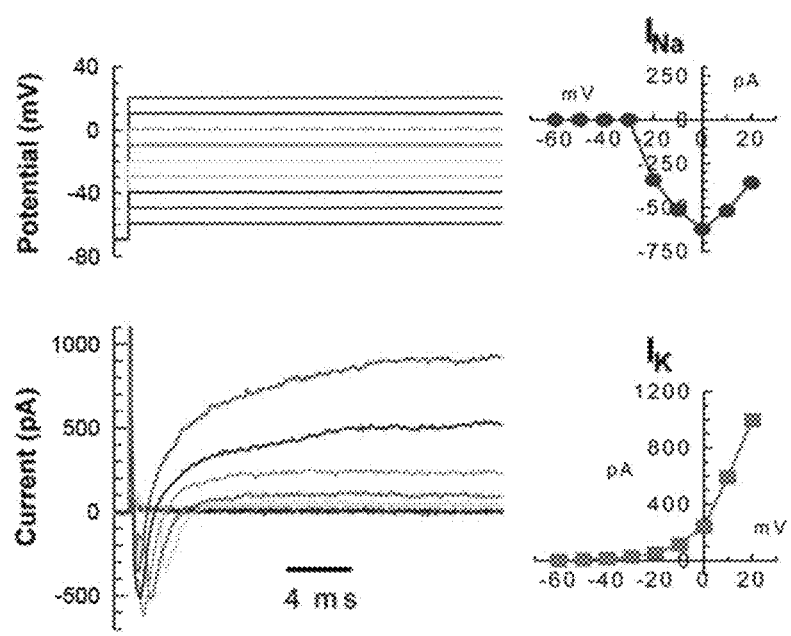
Figure 3B:
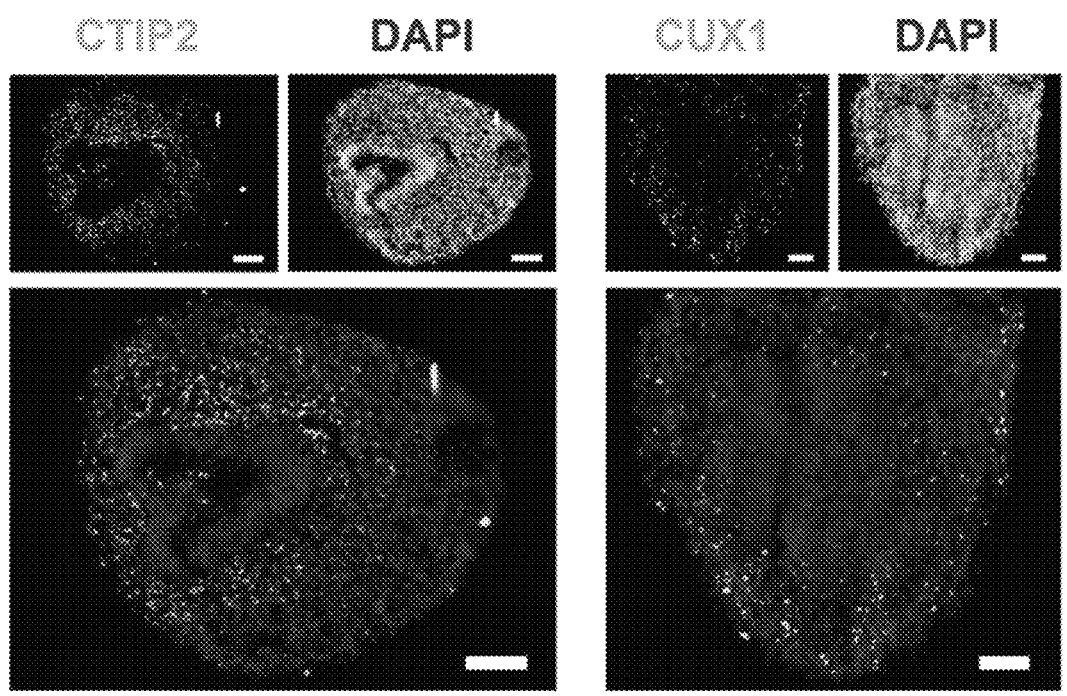

Early stage neocortical organoids (day 38) included large, proliferating polarized neuroepithelia, with ventricle-like cavities at the centers. The apical-end markers, N-cadherin, CD133, and gamma-tubulin were localized to the center of each organoid, facing the lumen (FIG. 2F-2H). PH3 (phosphorylated histone H3), a marker for the G2/M phase of the cell cycle, was detected in the apical zone (FIG. 2I). On day 38, early-born preplate TBR1$^+$ neurons were primarily located in TUJ1$^+$ areas surrounding the dorsopallial neuroepithelia (FIG. 2I-2J). REELIN$^+$ cells were also found in the most superficial layer of the TBR1$^+$ zone, which is likely indicative of Cajal-Retzius cells, which are involved in the generation of the cortical plate (FIG. 2K). At the end of differentiation at day 66, the TUJ1$^+$ mitotic zone became thicker (FIG. 2L), and both early cortical plate CTIP2$^+$ neurons and late cortical plate CUX1$^+$ neurons were present. The CTIP2$^+$ neurons were primarily located adjacent to the neuroepithelia; however, the CUX1$^+$ neurons were located evenly throughout the TUJ1$^+$ area (FIG. 3B), suggesting initiation of spatial separation of early and late cortical plate neurons. Intact-organoid immunohistochemistry using the newly-developed CLARITY method (Tomer et al., *Nat. Protoc.* 9:1682-1697, 2014) allowed antibodies, in this case BF1 and TUJ1, to label throughout the intact neocortical organoid, providing an alternative method for analysis of organoid cytoarchitecture (FIGS. 4A-4D).

Figure 3C:
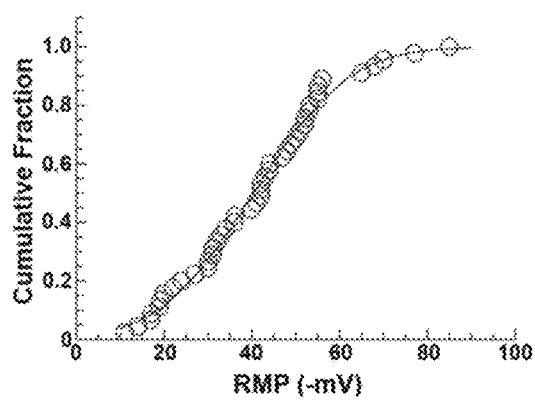
Figure 3D:
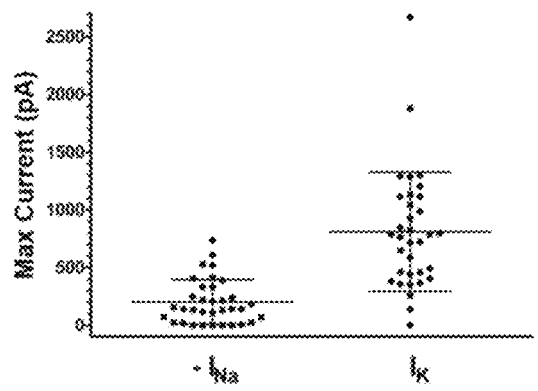
Figure 4D:
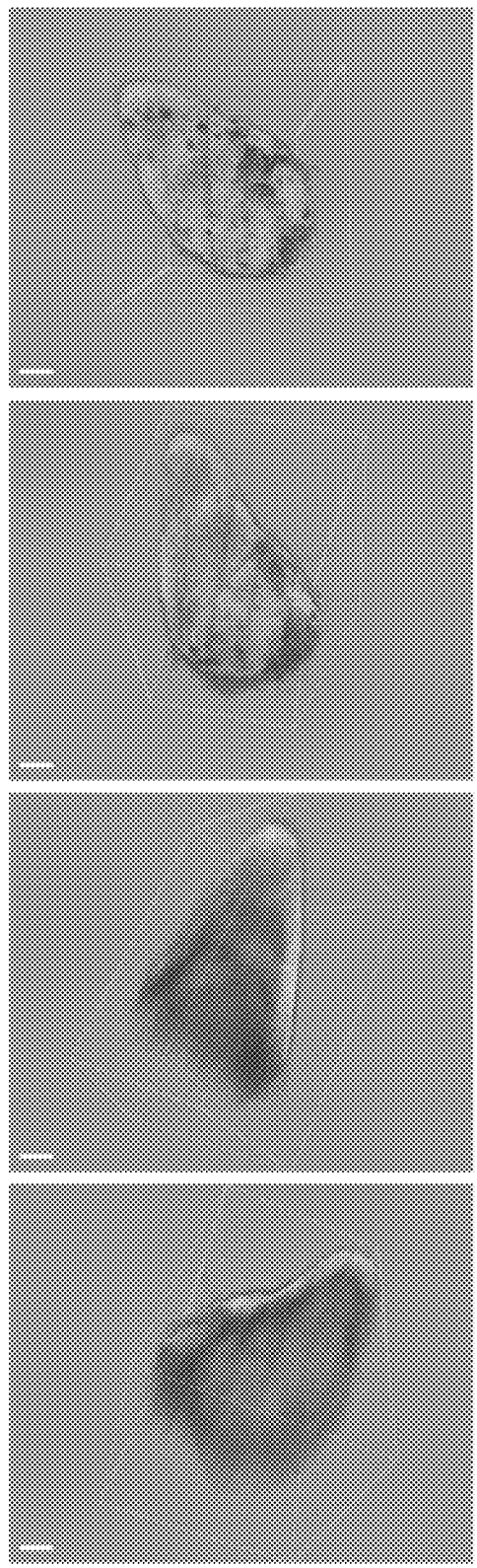

Conventional whole cell patch-clamp recording was used to evaluate the functional activity of the differentiated neocortical neurons. At day 66, cells held under current clamp condition exhibited robust action potentials. Correspondingly, large voltage-gated sodium currents and delayed rectifier potassium currents were revealed under voltage clamp conditions (FIGS. 2M-2P; FIGS. 3C-3D). Taken together, these data suggest that blockade of dual SMAD and FGF signaling at the start of differentiation induced formation of self-organized neocortical organoids, mimicking in vivo neocortical cytoarchitectural organization, and resulted in the establishment of functional neocortical neurons.

Example 2

Expression and Function of CYP3A5 and CYP3A43 in Neocortical Organoids

This example expression of CYP3A5 and CYP3A43 in neocortical organoids and the effect of CYP3A5 and CYP3A43 on cocaine-induced alterations in neocortical organoid development.

Methods

RT-PCR and RT-qPCR:

Total RNA was extracted from hPSCs at different stages of neocortical differentiation using RNA STAT-60 (Tel-Test) and subsequently treated with TURBO DNase (Ambion) to remove residual genomic DNA (Lee et al, *Cell Rep.* 10:616-632, 2015). RT-PCR and RTqPCR were employed to analyze and quantify gene expression, respectively, using cDNA synthesized from DNase-treated RNA (Transcriptor First Strand cDNA Synthesis Kit; Roche).

RT-PCR:

RT-PCR was performed using the QIAGEN Multiplex PCR Kit (QIAGEN) according to manufacturer's instructions. Primers for CYP3A isoforms were based on published literature (Williams et al, *J. Pharmacol. Exp. Ther.* 311:728-735, 2004). Negative controls were performed by omitting cDNA samples, primers, or polymerase during RT-PCR. Primer sequences are shown in Table 1.

RT-qPCR:

RT-qPCR was performed and analyzed with the LightCycler 480 Real-Time PCR System (Roche) using LightCycler 480 probes Master as described previously (Kindberg et al, *Dis. Model Mech.* 7:1397-1405, 2014). Primers, probes, and reference genes (Table 1) were designed using Universal ProbeLibrary Assay Design Center (Roche) and their specificities were confirmed by standard and melting curve validation. Measurements were performed in duplicate in two separate runs of three independent biological samples at each data point, and all results were normalized to a reference gene, which did not differ between samples. Quantification was performed using the comparative CT method. RT-qPCR of CYP3A5 and CYP3A43 was accomplished using the LightCycler® 480 SYBR Green I Master with LightCycler 480 Real-Time PCR System (Roche) following the manufacturer's instructions. Measurements were performed in duplicate in two separate runs of 3-5 independent biological samples, and all results were normalized to GAPDH, which did not differ between samples.

TABLE 1

RT-PCR and RT-qPCR primers

| Gene | Accession No. | Sequence (5'-3') | Fragment Size | SEQ ID NO: |
|------|---------------|------------------|---------------|------------|
| CYP3A4 | NM_017460.5 | F TGTTTCCAAGAGAAGTTACAAATTTTT | 91 bp | 1 |
|  |  | R TCCACTCGGTGCTTTTGTGT |  | 2 |
| CYP3A5 | NM_000777.4 | F ACTGAGTCCCACAAAGCTCTGT | 71 bp | 3 |
|  |  | R TAGCCAGCAAAAATGAAGATTATTG |  | 4 |

TABLE 1-continued

RT-PCR and RT-qPCR primers

| Gene | Accession No. | Sequence (5'-3') | Fragment Size | SEQ ID NO: |
|---|---|---|---|---|
| CYP3A7 | NM_000765.4 | F GGCCCACACCTCTGCC | 66 bp | 5 |
| | | R TGTCAAACGTCCAATAGCCC | | 6 |
| CYP3A43 | NM_022820.1 | F TGCTCTCACAAACATAAAACTTGCT | 85 bp | 7 |
| | | R CAGTGGGATCTGAGTCTCTTTACAA | | 8 |
| GAPDH | NM_001289746.1 | F ACCACAGTCCATGCCATCAC | 452 bp | 9 |
| | | R TCCACCACCCTGTTGCTGTA | | 10 |
| NANOG | NM_024865.2 | F CCCAGCCTTTACTCTTCCT | | 11 |
| | | R GAGAAGGCGAAATCCGAAG | | 12 |
| OCT4 | NM_002701.4 | F CTTCGCAAGCCCTCATTTC | | 13 |
| | | R GAGAAGGCGAAATCCGAAG | | 14 |
| T | NM_001270484.1 | F ACAGCGCATGATCACCAG | | 15 |
| | | R TTTGCAAATGGATTGTACTTAATTTT | | 16 |
| SOX17 | NM_022454.3 | F CGCCGAGTTGAGCAAGAT | | 17 |
| | | R GGTGGTCCTGCATGTGCT | | 18 |
| Nestin | NM_006617.1 | F TGGCGGTGGGGTCCTCACTGTGCAAATGATAGGCTITC | | 19 |
| | | R TGTAGGCCCTGTTTCTCCTG | | 20 |
| OTX2 | NM_0.21728.3 | F AACCTCCCATGAGGCTGTAA | | 21 |
| | | R GGTGGACAGGTTCAGAGTCC | | 22 |
| PAX6 | NM_000280.4 | F GGCACACACACATTAACACACTT | | 23 |
| | | R GGTGTGTGAGAGCAATTCTCAG | | 24 |
| HOXB4 | NM_024015.4 | F CTGGATGCGCAAAGTTCAC | | 25 |
| | | R AGCGGTTGTAGTGAAATTCCTT | | 26 |
| NKX2.1 | NM_001079668.2 | F TCATTTGTTGGCGACTGG | | 27 |
| | | R TGCTTTGGACTCATCGACAT | | 28 |
| LMX1A | NM_001174069.1 | F AGCATTCAAGGCCTCATTTG | | 29 |
| | | R GACGACACGGACACTCAGC | | 30 |

Analysis of Endogenous ROS Formation:

Endogenous ROS were measured by incubating neocortical organoids at day 44 with 100 μM 2',7'-dichlorofluorescein diacetate (DCFH-DA) (Sigma-Aldrich) for 30 min with or without cocaine. The organoids were washed and dissolved in 1% Triton X-100 in PBS. Fluorescence for each sample was measured at an excitation wavelength of 485 nm, and an emission wavelength of 530 nm using a fluorescence microplate reader (Techan Genios). Protein concentration for each sample was determined using the BCA assay (Pierce BCA® Protein Assay Kits; Thermo Scientific), according to manufacturer's instructions. The level of endogenous ROS for each sample was determined by dividing the fluorescence units by the concentration of protein in the lysate.

Knockdown Vectors:

Plasmid shRNA kits for CYP3A5 (Origene#TG313588) and CYP3A43 (Origene#TG305123), containing four different shRNAs for each gene, were tested. shRNA efficiency was examined for gene expression by transient transfection into HEK293 cells. The U6 promoter-shRNA cassettes that gave maximal knockdown for CYP3A5 (TG313588B-AACTGCATTGGCATGAGGTTTGCTCTCAT; SEQ ID NO: 31) and CYP3A43 (TG305123B-GTACTGGACAGAGCCTGAGAAGTTCTGCC; SEQ ID NO: 32), as well as the coding region for eGFP, were amplified by PCR and recombined using In-Fusion cloning mix (Clontech) into pLenti6.3/V5-DEST (Invitrogen) that had been digested with BamHI and MluI restriction enzymes. A control vector was similarly produced using the U6 promoter and a scrambled shRNA (Origene #TR30013). The resulting three vectors, pLenti6.3 CMV eGFP U6 shRNA (CYP3A5, Addgene #61266), pLenti6.3 CMV eGFP U6 shRNA (CYP3A43, Addgene #61265), and pLenti6.3 CMV eGFP U6 shRNA (nonspecific, Addgene #50951), were sequence verified and used to produce lentiviral particles. All lentiviral packaging plasmids were grown in the Stbl3 strain of E. coli (Invitrogen) to minimize recombination of the long terminal repeats.

Production and Titering of Lentivirus:

All lentiviral production and experimentation was conducted using Biosafety Level 2 procedures. Lentiviral vectors were packaged according to manufacturer's instructions using the Virapower Packaging system (Invitrogen) which produces replication-defective, VSVG pseudotyped, HIV-1 based lentiviral vector particles. Viral particles were purified and concentrated as described (Lee et al, Cell Rep. 10:616-632, 2015). Briefly, on the third day after transfection of packaging plasmids into 293FT cells, 20 ml of media was cleared by centrifugation for 5 min×1000 rpm followed by filtration through a 0.45 µm filter. The filtrate was centrifuged (22,000 rpm in Beckman 28S rotor, 4° C. for 2 h) through 2 ml of 20% sucrose cushion. The supernatant was aspirated and the viral pellet resuspended in 150 µl of cold HBSS over a 1 h period. Viral particles were aliquoted and frozen at −80° C. Titering of viral particles was performed using the Lenti-X p24 Rapid Titer Kit (Clontech) according to the manufacturer's instructions. Titers were measured as ng p24/ml and converted to infectious units per ml (IFU) as described in the manual for the Lenti-X p24 Rapid Titer Kit using 500 LP/IFU.

Lentiviral Transduction:

Neocortical organoids were plated in either 24-well or 96-well plates for viral infection. Cells were infected by adding 10 µl to each 24-well plate or 2.5 µl to each 96-well plate with a preparation containing 5×106 IFU/ml viral particles. Viral particles were added once to each preparation, at day 28, 4 days prior to the cocaine treatment, and removed at the next change of medium.

Results

The specific CYP450 enzymes responsible for the oxidative metabolism of cocaine vary between species, including CYP2A, 2B and 3A in mice, or CYP2B and 3A in rats. In humans, only the CYP3A family metabolizes cocaine (Valente et al, Curr. Med. Chem. 19:5601-5606, 2012). There are four isoforms of human CYP3A: CYP 3A4, 3A5, 3A7, and 3A43. CYP3A4, the predominant isoform of CYP3A, and CYP3A5 are primarily expressed in the adult liver and small intestine. Nevertheless, CYP3A4 and CYP3A5 proteins and mRNA have been identified in the adult human brain, and their potential role in the metabolism of endo- and xenobiotics in the brain have been emphasized (Booth Depaz et al, Drug Metab. Dispos. 41:1187-1194, 2013; McFadyen et al, Biochem. Pharmacol. 55:825-830, 1998). CYP3A7, primarily seen in the fetal liver, is sometimes expressed in the mature liver in small amounts. Lastly, CYP3A43 is expressed in small amounts in the liver, but is expressed at higher levels in the brain. Due to low levels of expression in the liver, CYP3A43 has not been thought to play a critical role in drug metabolism; however, CYP3A43 may play a role in the metabolism of drugs in the human brain (Agarwal et al, PLoS One 3:e2337, 2008).

Figure 5A:
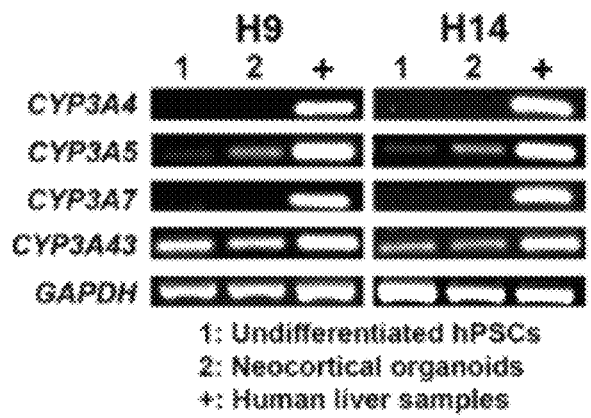
FIGS. 5A-5I is a series of panels showing neurodevelopmental effects of cocaine mediated by CYP3A5.

Due to the temporally sensitive effects of cocaine in rats, with neocortical abnormalities observed only when cocaine is administered during the most active period of neural progenitor proliferation (Lee et al, Synapse 65:21-34, 2011), the expression of CYP3A4, CYP3A5, CYP3A7, and CYP3A43 was examined at the undifferentiated hPSC stage and in the neocortical organoids at day 44, during which time the neuroepithelium is rapidly proliferating (FIG. 5A). CYP3A5 was expressed predominantly at the neocortical organoid stage, while CYP3A43 was expressed during both the undifferentiated and organoid stage (FIG. 5A). Expression of CYP3A4 and CYP3A7 was not detected at either stage (FIG. 5A). These data pinpoint CYP3A5 and CYP3A43 as prospective candidates for the metabolism-mediated developmental effects of cocaine.

Figure 5B:
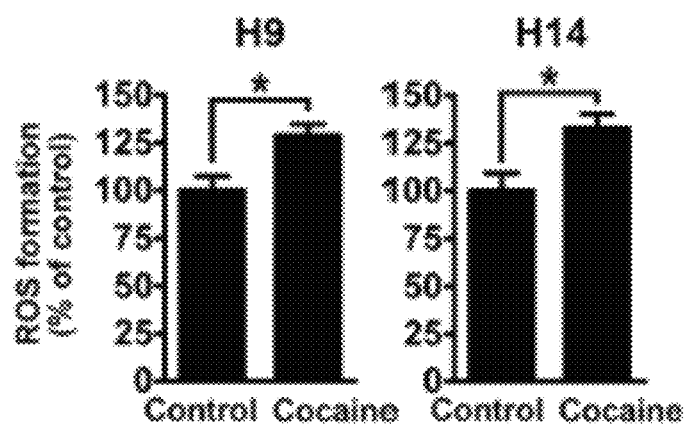
Figure 5C:
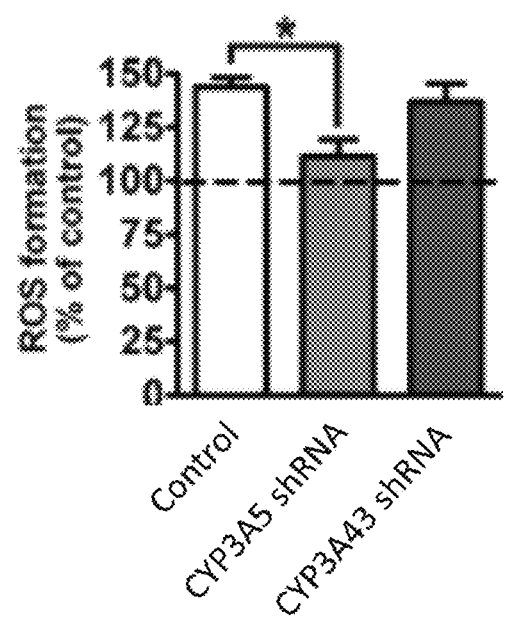
Figure 5D:
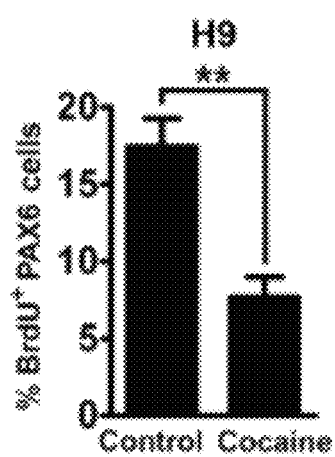
Figure 5E:
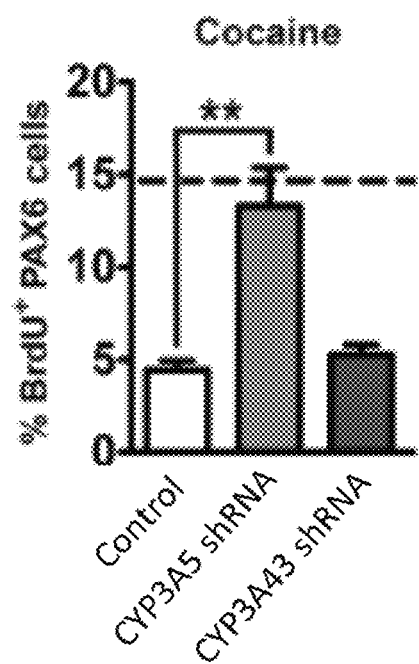
Figure 5F:
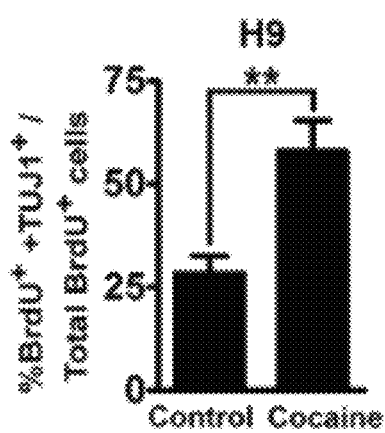
Figure 5G:
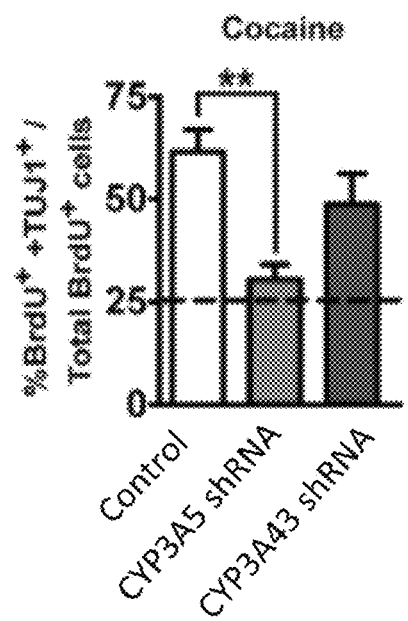
Figure 5H:
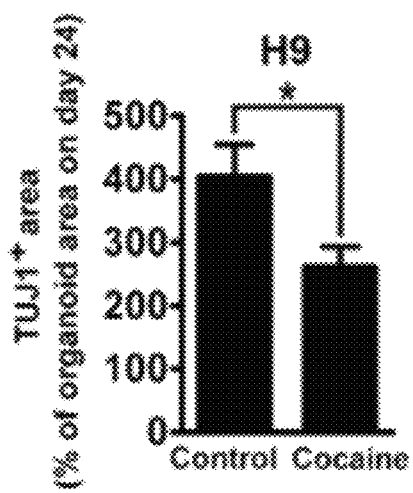
Figure 6A:
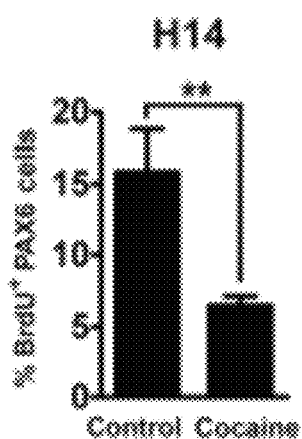
FIGS. 6A-6C are a series of graphs showing effects of cocaine on development of neocortical organoids treated with 3 μM cocaine for 1 hour every other day from days 32-44.
Figure 6B:
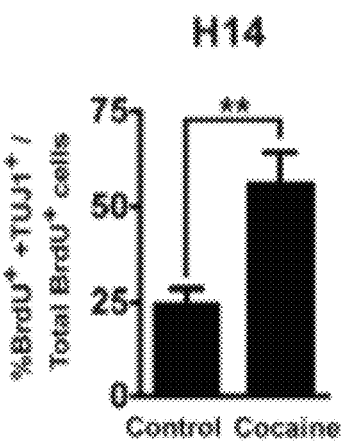
Figure 6C:
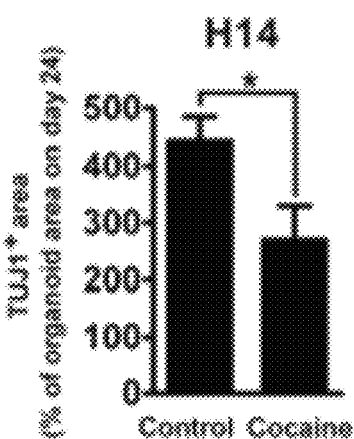

Taking into consideration that cocaine concentrations in the fetal rat neocortex drop rapidly to negligible levels 1 h after cocaine administration (Lee et al, PLoS Med. 5:e117, 2008), and to create a physiologically-meaningful drug treatment schedule in vitro, the neocortical organoids were exposed to a pharmacologically-relevant dose of cocaine, 3 µM (Kindberg et al, Dis. Model Mech. 7:1397-1405, 2014), for 1 h every other day, from days 32-44. This represents the most active period of proliferation of the neuroepithelium in these organoids (FIG. 2G). ROS generation in neocortical organoids was measured on day 44 and cocaine-induced ROS accumulation was observed (FIG. 5B). Cocaine also inhibited proliferation of PAX6$^+$ NE cells in neocortical organoids at day 45 (FIG. 5D and FIG. 6A). In the present model, post-mitotic neurons migrated toward the periphery of the NE. Neurogenesis was examined using BrdU pulse-chase experiments (1 h BrdU pulse, 24 h chase) from days 51-52, which showed that cocaine increased the migration of BrdU-labeled TUJ1 neurons outwards to the periphery of the NE area (FIG. 5F). The percentage of BrdU$^+$ cells that expressed TUJ1 was increased by cocaine as compared to control (FIG. 5F and FIG. 6B). These data suggest that cocaine exposure led to premature neuronal differentiation. Lastly, on day 66, at the end of differentiation, cocaine significantly inhibited development of the TUJ1$^+$ area (FIG. 5H and FIG. 6C). These data demonstrate that three-dimensional neocortical organoids can recapitulate cocaine-induced developmental abnormalities of the human neocortex.

Figure 5I:
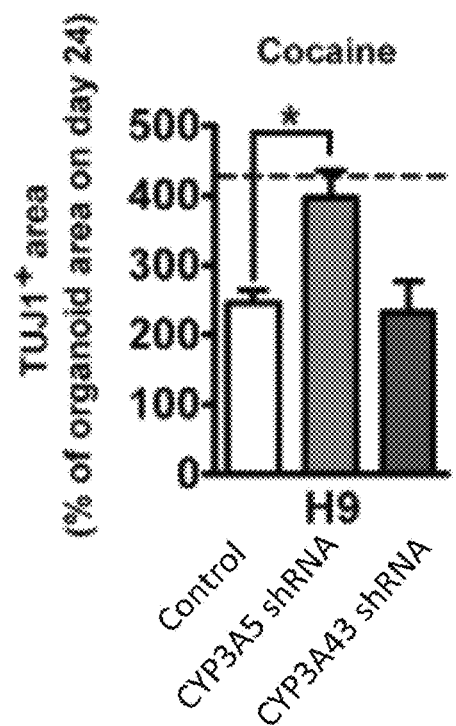
Figure 7:
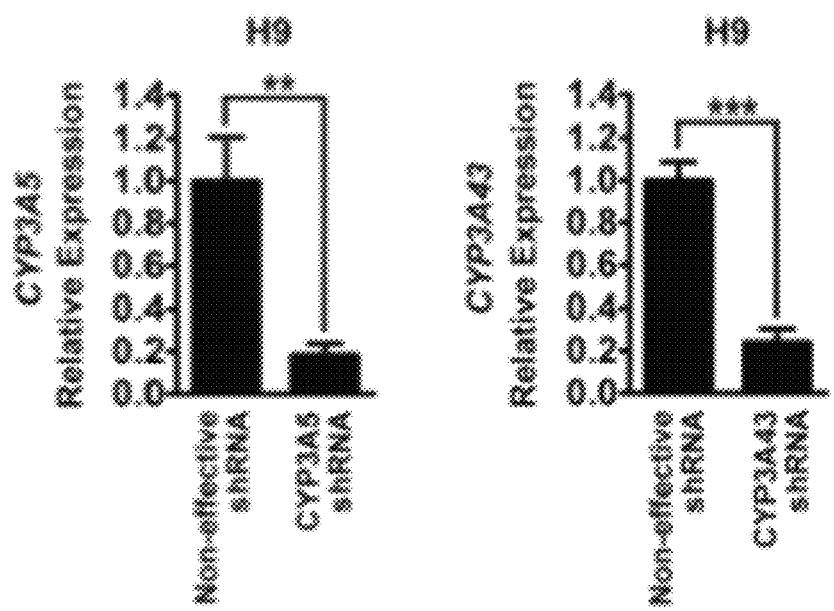
FIG. 7 is a pair of graphs showing lentivirus-mediated CYP3A5 (left) or CYP3A43 (right) knockdown in H9 through delivery of shRNAs at day 28 and relative expression was determined at day 32. n=5. Data are shown as means±SEM. Unpaired two-tailed Student's t-test. P<0.01 and *P<0.001.

To explore the role of CYP3A5 and CYP3A43 in these effects, lentiviral vectors were employed to deliver shRNA to silence either CYP3A5 or CYP3A43 using the H9 hESC line (FIG. 7). Knockdown of CYP3A5, but not CYP3A43, reversed cocaine-induced ROS generation (FIG. 5C), proliferation inhibition (FIG. 5E), and premature neuronal differentiation (FIG. 5G). The overall inhibition of neural tissue development by cocaine was reversed only by CYP3A5 knockdown (FIG. 5I). Moreover, knockdown of CYP3A5 or CYP3A43 itself did not interfere with neocortical development (FIGS. 8A-8D). These data indicate that CYP3A5, predominantly expressed during the beginning phase of neocorticogenesis, plays a dominant role in the adverse effects of cocaine in developing neocortical organoids.

Figure 9A:
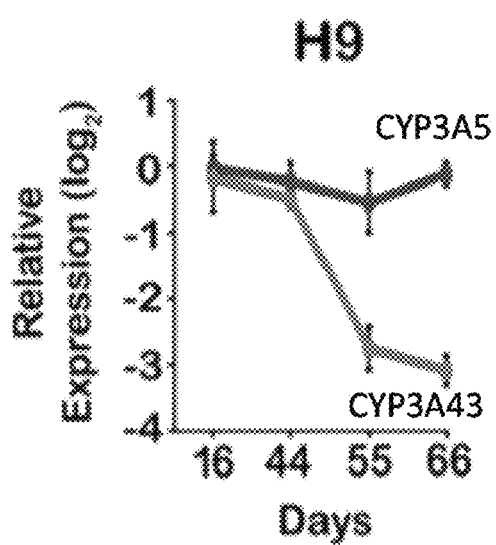
FIGS. 9A and 9B are a pair of graphs showing time course of gene expression for CYP3A5 and CYP3A43 at different stages of neocortical organoid differentiation in H9 (FIG. 9A) and H14 (FIG. 9B). n=3. Data are shown as means±SEM.
Figure 9B:
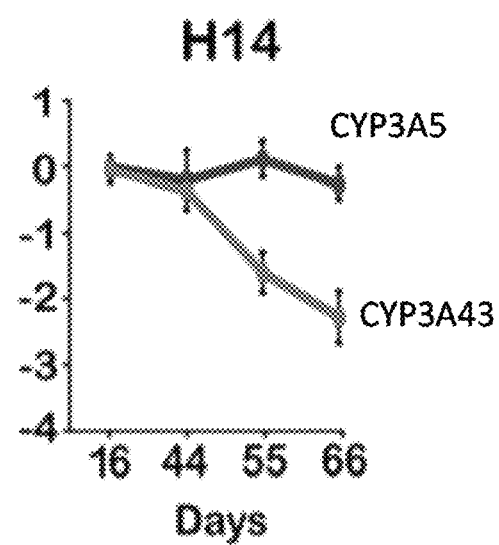

Both CYP3A5 and CYP3A43 were expressed in dorsal forebrain cortical progenitors at day 16 at levels similar to those seen during early neocorticogenesis at day 44 (FIG. 9A). Expression of CYP3A5 rapidly decreased after day 44 when neuronal differentiation gradually became dominant, while expression of CYP3A43 was maintained at a similar level until the end of differentiation (FIG. 9B). These data lend further support to the hypothesis that the neocortex is most vulnerable to cocaine during early neocorticogenesis.

Cocaine primarily alters neocortical development if administered when the neocortical organoids are still composed mainly of proliferative NE cells with high levels of CYP3A5 expression.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of culturing human embryonic stem cells or human induced pluripotent stem cells to produce a neocortical organoid, comprising:
   culturing human embryonic stem cells or human induced pluripotent stem cells in the presence of LDN193189, SB431542, and PD0325901 to form an embryoid body;
   culturing the embryoid body in adherent culture conditions in neural media comprising bFGF to form a neuroepithelial rosette;
   isolating the neuroepithelial rosette and placing the rosette in suspension culture in the presence of bFGF and FGF18 to produce cells with dorsal cortical identity; and
   culturing the cells with dorsal cortical identity in neurobasal medium in the absence of added trophic factors to form a neocortical organoid.

2. The method of claim 1, wherein the human embryonic stem cells or human induced pluripotent cells are cultured in the presence of LDN193189, SB431542, and PD0325901 for 1 to 6 days.

3. The method of claim 1, wherein the human embryonic stem cells or human induced pluripotent cells are cultured in the presence of 0.01-1 µM LDN193189 and 1-100 µM SB431542.

4. The method of claim 3, wherein the human embryonic stem cells or human induced pluripotent cells are cultured in the presence of 0.1 µM LDN193189 and 10 µM SB431542.

5. The method of claim 1, wherein the human embryonic stem cells or human induced pluripotent cells are cultured in the presence of 1-100 µM PD0325901.

6. The method of claim 5, wherein the human embryonic stem cells or human induced pluripotent cells are cultured in the presence of 10 µM PD0325901.

7. The method of claim 1, wherein the embryoid body is cultured with the bFGF for 2-21 days.

8. The method of claim 7, wherein the embryoid body is cultured in the presence of 10-50 ng/ml bFGF.

9. The method of claim 1, the isolated neuroepithelial rosette is 10,000 µm$^2$ to 100,000 µm$^2$.

10. The method of claim 9, wherein the isolated neuroepithelial rosette is at least 50,000 µm$^2$.

11. The method of claim 1, wherein the rosette is placed in suspension culture in the presence bFGF and FGF18 for 5-10 days.

12. The method of claim 11, wherein the rosette is placed in suspension culture in the presence of 10-50 ng/ml bFGF and 10-50 ng/ml FGF18.

13. The method of claim 12, wherein the rosette is placed in suspension culture in the presence of 20 ng/ml bFGF and 20 ng/ml FGF18.

14. The method of claim 1, wherein the cells with dorsal cortical identity are cultured in the absence of added trophic factors for three weeks or more.

15. A method of culturing human embryonic stem cells or human induced pluripotent cells to produce a neocortical organoid, comprising:
   culturing human embryonic stem cells or human induced pluripotent cells in the presence of 0.1 µM LDN193189, 10 µM SB431542, and 10 µM PD325901 for 1 to 6 days to form an embryoid body;
   culturing the embryoid body in adherent culture conditions in neural media comprising 20 ng/ml bFGF for 2-21 days to form a neuroepithelial rosette of at least 50,000 µm$^2$;
   isolating the neuroepithelial rosette and placing the rosette in suspension culture in the presence of 20 ng/ml bFGF and 20 ng/ml FGF18 to produce cells with dorsal cortical identity; and
   culturing the cells with dorsal cortical identity in neurobasal medium in the absence of added trophic factors for at least three weeks to form a neocortical organoid.

* * * * *